(12) United States Patent
Shigemori

(10) Patent No.: US 8,279,274 B2
(45) Date of Patent: Oct. 2, 2012

(54) RECEIVING APPARATUS, TRANSMITTING APPARATUS AND IN-VIVO INFORMATION ACQUIRING APPARATUS

(75) Inventor: Toshiaki Shigemori, Hachioji (JP)

(73) Assignee: Olympus Corporation, Tokyo (JP)

( * ) Notice: Subject to any disclaimer, the term of this patent is extended or adjusted under 35 U.S.C. 154(b) by 1614 days.

(21) Appl. No.: 11/661,952

(22) PCT Filed: Apr. 10, 2006

(86) PCT No.: PCT/JP2006/007574
§ 371 (c)(1),
(2), (4) Date: Mar. 2, 2007

(87) PCT Pub. No.: WO2006/134714
PCT Pub. Date: Dec. 21, 2006

(65) Prior Publication Data
US 2007/0252893 A1 Nov. 1, 2007

(30) Foreign Application Priority Data

Jun. 14, 2005 (JP) ................................. 2005-174018

(51) Int. Cl.
*H04N 7/18* (2006.01)
*A61B 1/04* (2006.01)
*H04N 7/00* (2011.01)
*H04L 27/06* (2006.01)

(52) U.S. Cl. .......... 348/65; 348/463; 375/240; 375/343; 600/109

(58) Field of Classification Search .......................... None
See application file for complete search history.

(56) References Cited

U.S. PATENT DOCUMENTS

| | | | | |
|---|---|---|---|---|
| 4,424,532 A | * | 1/1984 | den Toonder et al. | 380/226 |
| 5,103,308 A | * | 4/1992 | Asano | 348/441 |
| 5,168,246 A | * | 12/1992 | Pulluru et al. | 331/8 |
| 5,664,045 A | * | 9/1997 | Park | 386/264 |
| 5,712,624 A | * | 1/1998 | Ayerst et al. | 340/7.22 |
| 6,754,280 B2 | * | 6/2004 | Nguyen | 375/240.28 |
| 7,336,738 B2 | * | 2/2008 | Wakamatsu | 375/343 |
| 7,440,765 B2 | * | 10/2008 | Lanzone et al. | 455/502 |
| 2004/0196364 A1 | | 10/2004 | Takahashi | |
| 2005/0004473 A1 | | 1/2005 | Fujita et al. | |

(Continued)

FOREIGN PATENT DOCUMENTS

JP 07/322089 12/1995

(Continued)

*Primary Examiner* — Wen-Tai Lin
(74) *Attorney, Agent, or Firm* — Scully, Scott, Murphy & Presser, P.C.

(57) ABSTRACT

To provide a transmitting apparatus, a receiving apparatus, and an in-vivo information acquiring system that enable to acquire image information corresponding to one image, by assuredly synchronizing between a capsule endoscope and the receiving apparatus. According to the present invention, a capsule endoscope 2 that transmits a radio signal including at least an image signal S to the receiving apparatus includes a signal processor 12 that outputs the image signal S, a reference signal generator 24 that generates a reference signal including a different signal level and outputs a reference signal component D including at least the reference signal, an inserting unit 14 that inserts the reference signal component D into a predetermined heading period of the image signal S and at least a portion of a blanking period in which a signal component does not exist, and a transmitting unit 15 that wirelessly transmits the image signal S output from the inserting unit 14 to an outside.

17 Claims, 19 Drawing Sheets

U.S. PATENT DOCUMENTS

2007/0055099 A1 3/2007 Kimoto

FOREIGN PATENT DOCUMENTS

| | | |
|---|---|---|
| JP | 2001-231186 | 8/2001 |
| JP | 2004-167163 | 6/2004 |
| JP | 2004-305372 | 11/2004 |
| JP | 2004-305373 | 11/2004 |
| JP | 2005-260751 | 9/2005 |
| JP | 2005-319097 | 11/2005 |
| WO | WO 2005/065525 A1 | 7/2005 |

* cited by examiner

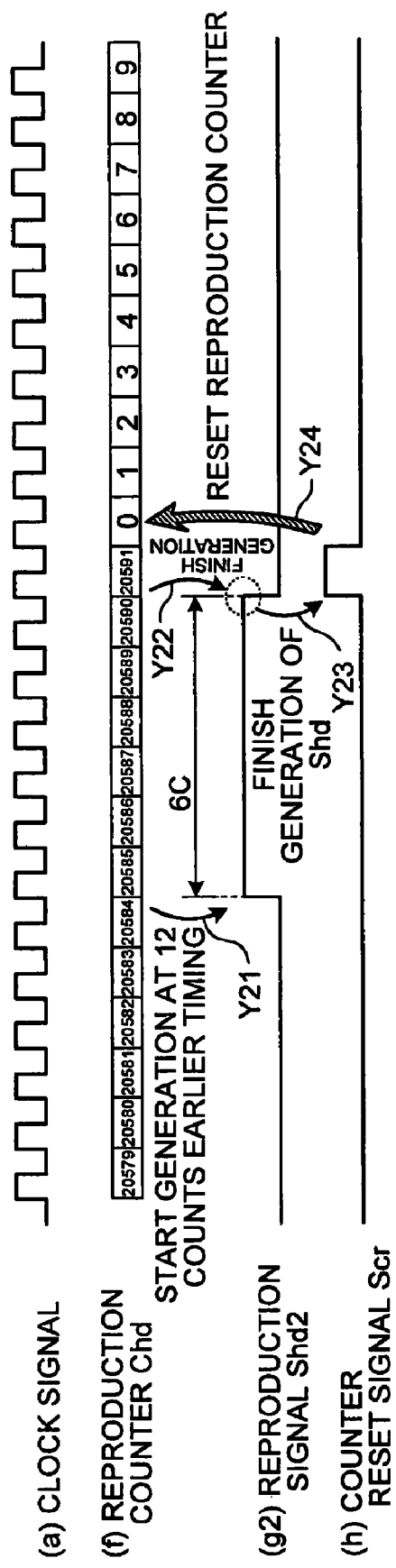

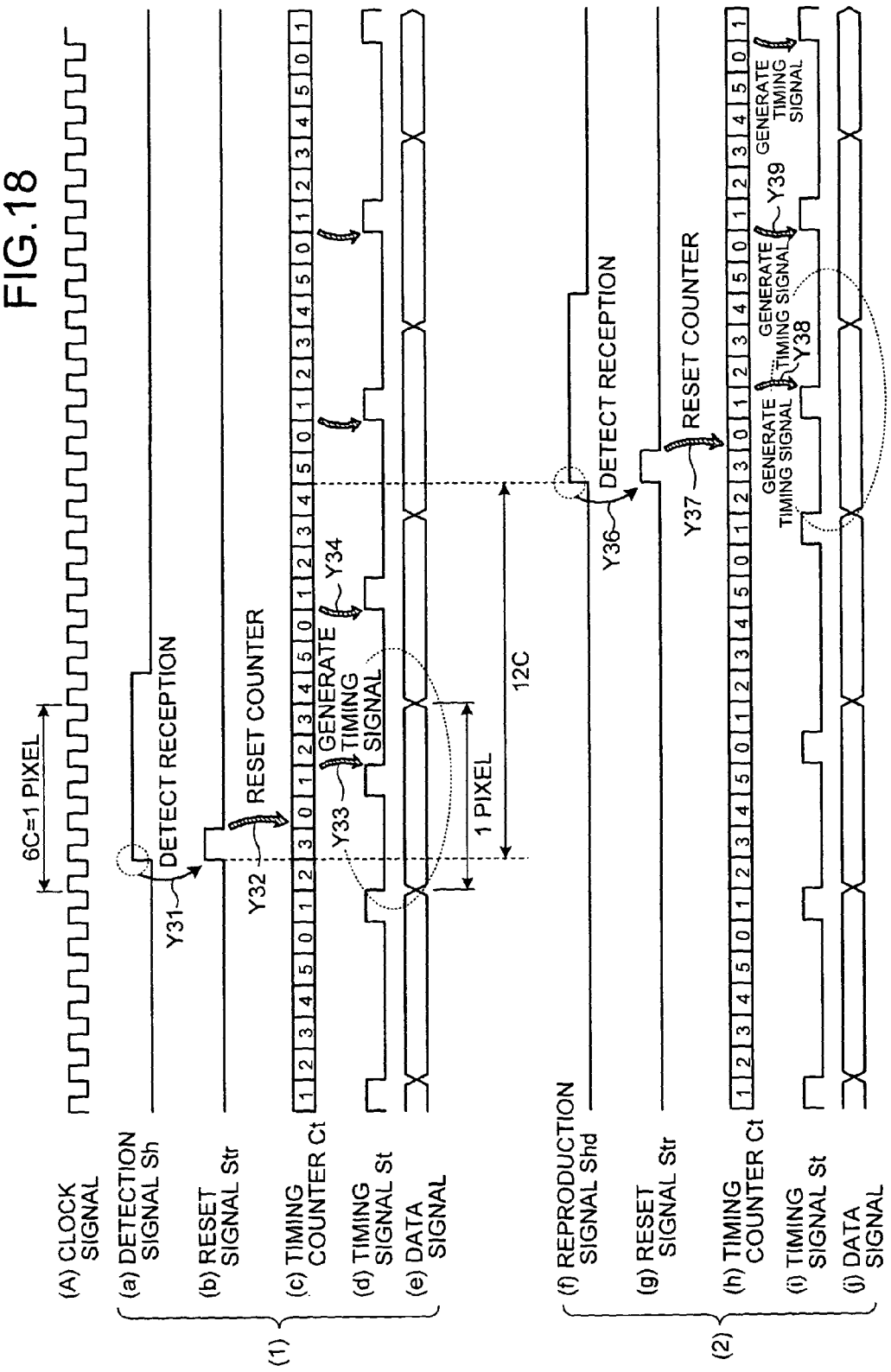

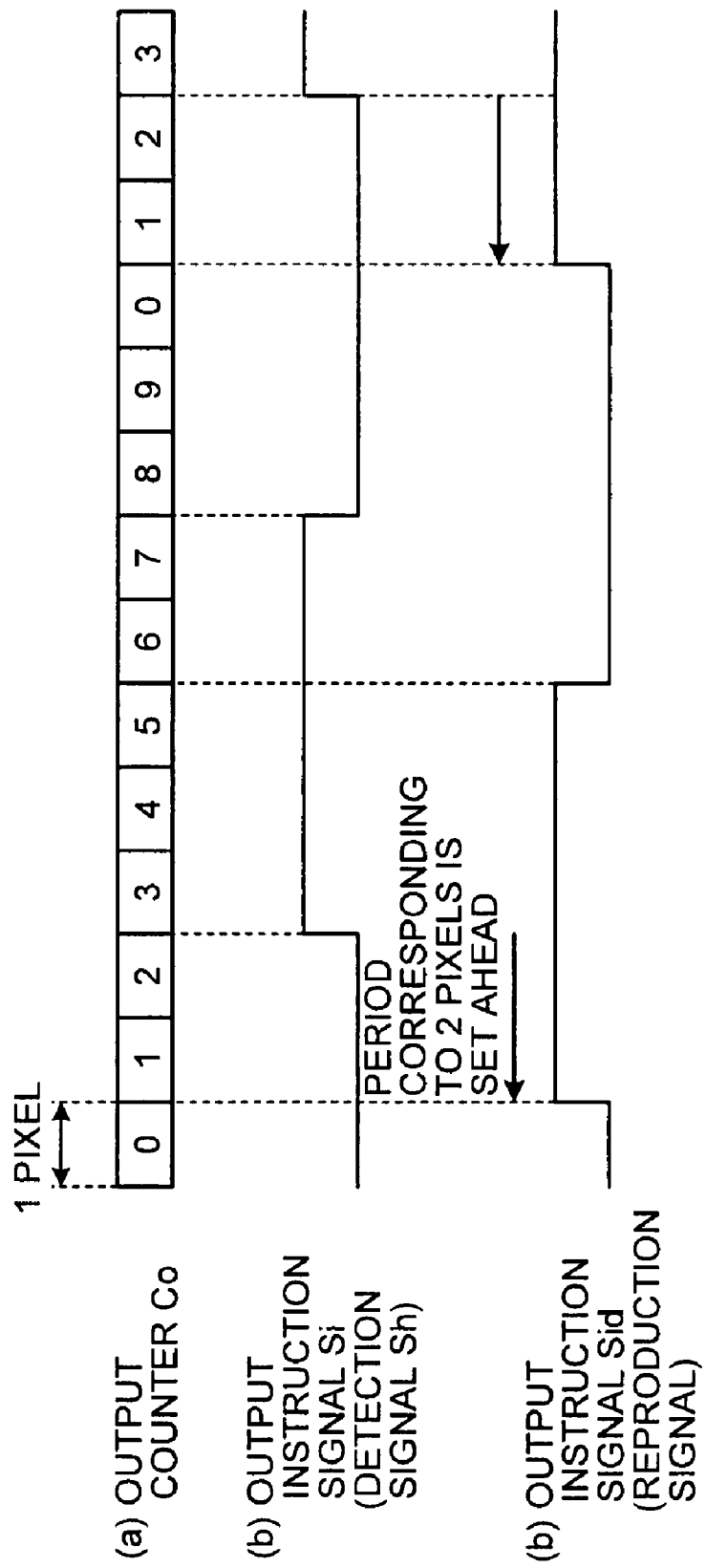

RECEIVING APPARATUS, TRANSMITTING APPARATUS AND IN-VIVO INFORMATION ACQUIRING APPARATUS

TECHNICAL FIELD

The present invention relates to a transmitting apparatus that transmits a radio signal including at least main frame portion of information to an outside, a receiving apparatus that processes the radio signal transmitted from the transmitting apparatus, and an in-vivo information acquiring system.

BACKGROUND ART

Recently, a capsule endoscope including an imaging function and a radio communication function has been proposed in the filed of an endoscope. The capsule endoscope includes a function to travel inside organs (inside of a body cavity) such as a stomach or a small intestine by a peristaltic movement to capture images one by one during an observation period from when the capsule endoscope is swallowed by an examinee as a subject for an observation (examination) until the capsule endoscope is naturally excreted from a body of the examinee.

During the observation period in which the capsule endoscope travels inside the organs, image data captured inside the body cavity by the capsule endoscope is sequentially transmitted to the outside of the subject, through the radio communication function such as a Bluetooth, and stored in a memory provided in an external receiving apparatus. By carrying the receiving apparatus including the radio communication function and a memory function, the examinee can move with less inconvenience during the observation period from when the examinee swallows the capsule endoscope until the capsule endoscope is excreted. After the observation is finished, a doctor or a nurse makes a diagnosis by displaying body cavity images on a display unit such as a display, based on the image data stored in the memory of the receiving apparatus (see, for example, Patent Document 1).

On the other hand, with a conventional capsule endoscope, in the capsule endoscope system, the image data captured by the capsule endoscope is transmitted by radio with a data configuration similar to that for an image transmission in, for example, a national television system committee (NTSC) format. In other words, with the conventional capsule endoscope, as an image data corresponding to one image, synchronous data including a vertical synchronous signal for synchronizing in a vertical direction, and scan line data of each of the scan lines that includes each of horizontal synchronous signals are transmitted in such a state that a so-called horizontal blanking period is provided between two pieces of the scan line data.

Patent Document 1: Japanese Patent Application Laid-Open No. 2001-231186 (Page. 3, FIG. 1)

DISCLOSURE OF INVENTION

Problem to be Solved By The Invention

However, with the conventional capsule endoscope, the receiving apparatus firstly detects a vertical direction of the image, that is, a heading portion, by using the vertical synchronous signal from among the data transmitted from the capsule endoscope, and thereafter, detects the horizontal synchronous signal for every scan line data, detects the heading of each of the scan lines, and processes each of the scan line data for acquiring the image information corresponding to one image. With the conventional capsule endoscope, an asynchronous mode is accepted in which the frequency of a radio signal transmitted from the capsule endoscope and the frequency of a reference signal at the side of the receiving apparatus are not synchronized. In this case, when the radio signal transmitted from the capsule endoscope is distorted by an external noise and the like during the transmission, because the frequency of a reference clock of the receiving apparatus and the frequency of the radio signal transmitted form the capsule endoscope are not synchronized, the receiving apparatus cannot detect the vertical synchronous signal. As a result, there are problems that the receiving apparatus cannot detect the heading of the image information with the vertical synchronous signal added, and cannot process the image information. Similarly, when the radio signal is distorted while the radio signal corresponding to one image is received, the receiving apparatus cannot detect the horizontal synchronous signal that is added to the heading of each of the scan lines. As a result, the receiving apparatus cannot perform the image process of the scan line data for which the horizontal synchronous signal is not detected. Therefore, the conventional receiving apparatus is forced to process the rest of scan line data for which the horizontal synchronous signal is not detected as the noise, and there is a problem that the one image corresponding to the image data cannot accurately acquired. As described, conventionally, not all the body cavity image captured by the capsule endoscope are provided to the doctor or the nurse, and there sometimes causes a problem to the accurate diagnosis made by the user.

The present invention is made in view of the above problems and an object of the present invention is to provide a transmitting apparatus, a receiving apparatus, and an in-vivo information acquiring system that enables to accurately acquire image information corresponding to one image, by assuredly synchronizing between a capsule endoscope and the receiving apparatus.

MEANS FOR SOLVING PROBLEM

A transmitting apparatus according to the present invention that transmits a radio signal including at least main frame portion of information to a receiving apparatus, the transmitting apparatus includes an information main-frame output unit that outputs the main frame portion of information; a reference signal generator that generates a reference signal including a different signal level and outputs a reference signal component including at least the reference signal; an inserting unit that inserts the reference signal component into a predetermined heading period of the main frame portion of information and at least a part of a blanking period in which a signal component does not exist, and outputs the main frame portion of information; and a radio transmitting unit that wirelessly transmits the main frame portion of information output from the inserting unit to an outside, wherein a frequency of the transmitted radio signal and a frequency of a process reference clock which is a process reference for the radio signal are synchronized in the receiving apparatus, by using the reference signal among the radio signal transmitted from the transmitting apparatus.

The transmitting apparatus according to the present invention may further include a selector that selects the frequency of the reference signal based on instruction information for instructing whether the reference signal component has been inserted and the frequency of the reference signal included in the reference signal component to be inserted, wherein the reference signal generator may generate the reference signal with the frequency selected by the selector.

The transmitting apparatus according to the present invention may further include a timing generator that controls an output timing of the main frame portion of information in the information main-frame output unit and correlates an output timing of the reference signal component in the reference signal generator with the predetermined heading period of the main frame portion of information output from the information main-frame output unit and at least a part of the blanking period.

The transmitting apparatus according to the present invention may further include a storage unit that stores the instruction information, wherein the selector may select whether the reference signal component has been inserted and the frequency of the reference signal included in the reference signal component to be inserted, based on the instruction information stored in the storage unit.

The transmitting apparatus according to the present invention may further include an information acquiring unit that acquires predetermined information to be a process target in the information main-frame output unit and outputs the acquired predetermined information to the information main-frame output unit, wherein the information main-frame output unit may process the information output from the information acquiring unit and thereafter outputs the processed information as the main frame portion of information, and the selector may select one of a frequency corresponding to a frequency of the main frame portion of information output from the information main-frame output unit and a frequency corresponding to a frequency of the predetermined information output from the information acquiring unit, as the frequency of the reference signal based on the instruction information.

In the transmitting apparatus according to the present invention, the main frame portion of information may be an image signal, the blanking period may be a horizontal blanking period, and the predetermined heading period may include a vertical synchronous signal.

In the transmitting apparatus according to the present invention, the transmitting apparatus may have a function for acquiring in-vivo information when inserted into a subject, and the main frame portion of information may be formed by including the in-vivo information.

A receiving apparatus according to the present invention that processes the information component among the radio signal received by an antenna, the receiving apparatus includes an antenna for receiving a radio signal including a predetermined unit of an information component that structures a main frame portion of information; a detector that detects a synchronous signal added to the information component with respect to each information component, generates a detection signal indicating a heading of the information component when the synchronous signal is detected, and generates a reproduction signal indicating the heading of the information component based on the previously generated detection signal when the synchronous signal is not detected; a timing signal output unit that outputs a timing signal that instructs a process start timing of the information component in response to an input timing of the information component, based on either the detection signal or the reproduction signal generated by the detector; and a processor that initiates a process of the information component in synchronization with the input timing of the information component, based on the timing signal output from the timing signal output unit.

In the receiving apparatus according to the present invention, the detector may output the detection signal when a portion larger than a predetermined portion is detected from the entire synchronous signal.

In the receiving apparatus according to the present invention, the detector may generate the reproduction signal when the synchronous signal is not detected during a period from when a previous detection signal is generated until the synchronous signal for a next information component is detected.

In the receiving apparatus according to the present invention, the timing signal output unit may set a first output of the timing signal generated based on the reproduction signal ahead of a first output of the timing signal generated based on the detection signal by a period for generating the reproduction signal by the detector.

In the receiving apparatus according to the present invention, the radio signal may include an image signal, the information component may be a scan line component that structures the image signal, and the synchronous signal may be a horizontal synchronous signal.

In the receiving apparatus according to the present invention, the radio signal may be formed by including in-vivo information acquired by a transmitting apparatus that is inserted into a subject.

An in-vivo information acquiring system according to the present invention includes a body insertable apparatus that is to be inserted into a body and transmits a radio signal including acquired information to an outside; and a receiving apparatus that receives the radio signal transmitted from the body insertable apparatus, wherein the body insertable apparatus contains an information main-frame output unit that outputs an main frame portion of information including acquired in-vivo information; a reference signal generator that generates a reference signal including a different signal level and outputs a reference signal component including at least the reference signal; an inserting unit that inserts the reference signal component into a predetermined heading period of the main frame portion of information and at least a part of a blanking period in which a reference signal component does not exist, and outputs the reference signal component; and a radio transmitting unit that wirelessly transmits the main frame portion of information output from the inserting unit to an outside, and the receiving apparatus contains a receiving antenna; and an external device that processes the main frame portion of information included in the radio signal received via the antenna, by using the reference signal component inserted into the main frame portion of information, wherein a frequency of the transmitted radio signal and a frequency of a process reference clock which is a process reference for the radio signal are synchronized by using the reference signal among the radio signal transmitted from the transmitting apparatus.

An in-vivo information acquiring system according to the present invention includes a body insertable apparatus that is to be inserted into a body and transmits a radio signal including acquired information to an outside; and a receiving apparatus that receives the radio signal transmitted from the body insertable apparatus, wherein the body insertable apparatus contains a signal output unit that outputs a signal that includes an acquired in-vivo information and that is added a process reference signal at a heading portion of each of predetermined signal components; and a radio transmitting unit that wirelessly transmits the signal output by the signal output unit to an outside, and the receiving apparatus contains an antenna that receives a radio signal including a predetermined unit of an information component that structures an main frame portion of information; a detector that detects a synchronous signal added to the information component with respect to each information component, generates a detection signal indicating a heading of the information component when the synchronous signal is detected, and generates a reproduction signal indicating the heading of the information component based on the previously generated detection signal when the synchronous signal is not detected; a timing signal output unit that outputs to the processor a timing signal that instructs a process start timing of the information component in response to an input timing of the information component, based on either the detection signal or the reproduction signal generated by the detector; and a processor that initiates a process of the information component in synchronization with the input timing of the information component, based on the timing signal output from the timing signal output unit.

EFFECT OF THE INVENTION

According to a transmitting apparatus of the present invention, a reference signal component including at least a reference signal that includes a different signal level is inserted into a main frame portion of information and is transmitted. The transmitting apparatus of the present invention selects whether the reference signal component is inserted. As a result, when the transmitting apparatus selects that the reference signal component is inserted, a receiving apparatus changes the frequency of a reference clock in response to the frequency of a transmitting signal transmitted from the transmitting apparatus, by using the reference signal, enables to synchronize between the frequency of a radio signal transmitted from the transmitting apparatus and the frequency of the reference clock of the receiving apparatus, and enables to accurately process the received radio signal regardless of whether a synchronous signal is detected. Further, according to the receiving apparatus of the present invention, even when the transmitting apparatus selects that the reference signal component is not inserted, if the synchronous signal cannot be detected from an information component of the received radio signal, a reproduction signal is generated based on a detection signal that is previously generated, and assuredly performs a process synchronization for the information component by using the reproduction signal, and therefore, the information component of the received radio signal can be accurately processed. As a result, according to the present invention, when a process target signal is an image signal, the image signal transmitted from the transmitting apparatus is accurately processed at the side of the receiving apparatus, and an image transmitted from the transmitting apparatus can properly be provided to a user.

BRIEF DESCRIPTION OF DRAWINGS

FIG. 17 is a timing chart for describing the reproduction-signal generation and the output process shown in FIG. 13;

FIG. 18 is a timing chart for describing a process operation of a timing signal generator shown in FIG. 12; and FIG. 19 is a timing chart for describing a process operation of the timing signal generator shown in FIG. 12

EXPLANATIONS OF LETTERS OR NUMERALS

Figure 1:
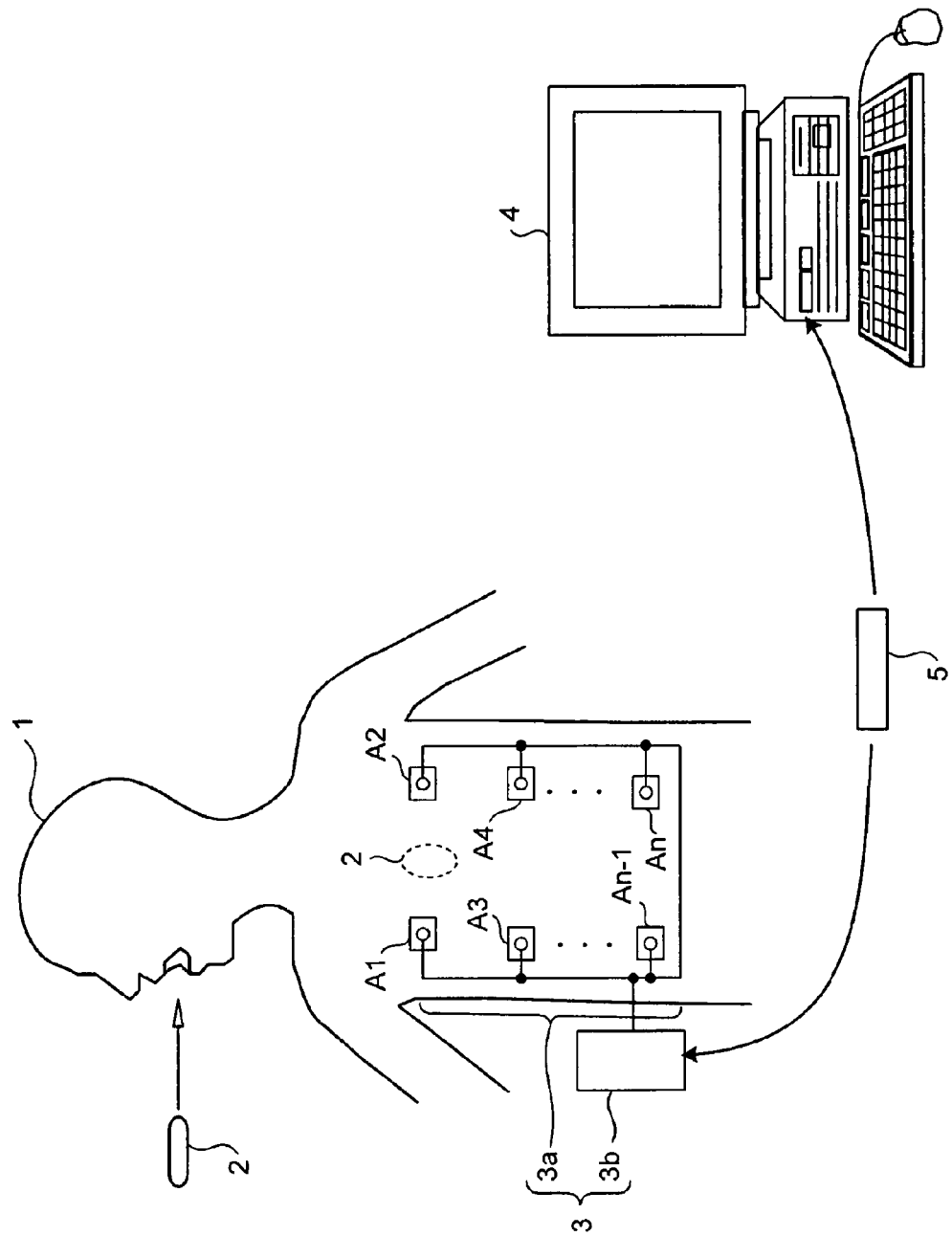
FIG. 1 is a schematic view of an entire configuration of an in-vivo information acquiring system according to a first embodiment of the present invention.

1 Subject
2, 202 Capsule endoscope
3, 203 Receiving apparatus
3a Antenna group
3b, 203b External device
4 Display device
5 Portable recording medium
11 In-vivo information acquiring unit
12 Signal processor
13 Reference-signal-component output unit
14 Inserting unit
15 Radio transmitting unit
16 Timing generator
17 Battery
18 Light emitting diode (LED)
19 LED driving circuit
20 Charge coupled device (CCD)
21 CCD driving circuit
22 Storage unit
23 Synchronous mode selector
24 Reference signal generator
25 Transmitting circuit
26 Transmitting antenna
31 Receiving unit
33 Converter
34, 234 Synchronous signal detector
35 Image processor
36 Controller
37 Storage unit
38 Power supply unit
39 Synchronization assuring unit
39a, 239a Reference clock
236 Horizontal-synchronous-signal detector
237 Reproducing unit
238 Timing signal generator
239 Synchronization controller BEST MODE(S) FOR CARRYING OUT THE INVENTION n Best exemplary embodiments (hereinafter, simply called "embodiments") of a transmitting apparatus, a receiving apparatus, and an in-vivo information acquiring system according to the present invention are described below in detail with reference to the accompanying drawings. The drawings are schematic views, therefore, it should be noted that a relation between a thickness and a width of each of portions and a ratio of the thickness between each of the portions are different from those in actual ones, and it is obvious that portions of which a relation or a ratio between each of sizes are different between the drawings are included. Further, for the description of the drawings, same reference numerals are assigned to same components. The embodiments are described with an example in which the transmitting apparatus and the receiving apparatus are applied to the in-vivo information acquiring system. However, it is needles to say that an application area for the transmitting apparatus and the receiving apparatus is not limitedly interpreted by the in-vivo information acquiring system.

(First Embodiment)

FIG. 1 is a schematic view of an entire configuration of the in-vivo information acquiring system that includes the transmitting apparatus and the receiving apparatus according to a first embodiment of the present invention. In FIG. 1, the in-vivo information acquiring system includes a capsule endoscope 2 that is to be inserted into a body cavity of a subject 1, captures a body cavity image, and transmits data such as an image signal to a receiving apparatus 3, and the receiving apparatus 3 that includes a radio receiving function. The in-vivo information acquiring system includes a display device 4 that displays a body cavity image based on a radio signal received by the receiving apparatus 3, and a portable recording medium 5 that transmits and receives data between the receiving apparatus 3 and the display device 4. The receiving apparatus 3 includes an antenna group 3a and an external device 3b that performs a process of the radio signal received by the antenna group 3a.

The display device 4 is for displaying and processing the body cavity image captured by the capsule endoscope 2, and includes, for example, a workstation that performs an image display and an image process based on the data obtained by the portable recording medium 5. The display device 4 can be configured to directly display an image by a cathode-lay tube (CRT) display or a liquid crystal display, or to output the image to other media such as a printer.

The portable recording medium 5 is removable to the external device 3b and the display device 4, and has a configuration that enables to output and record information when the portable recording medium 5 is inserted into the both devices. More specifically, while the capsule endoscope 2 travels inside the body cavity of the subject 1, the portable recording medium 5 is inserted into the external device 3b and records data transmitted from the capsule endoscope 2. It is configured so that, when the capsule endoscope 2 is excreted from the subject 1, that is, when an imaging of the inside of the subject 1 is finished, the portable recording medium 5 is removed from the external device 3b and inserted into the display device 4, and the recorded data is read out by the display device 4. For example, by performing a data transmission and a data reception between the external device 3b and the display device 4 by the portable recording medium 5 such as a compact flash® memory, the subject 1 can freely move while the body cavity image is captured, unlike such a case that the external device 3b and the display device 4 are directly connected via a wire. In the above description, the portable recording medium 5 is used for the data transmission and the data reception between the external device 3b and the display device 4. However, it is not thus limited and it is acceptable to have such a configuration that other built-in recording medium such as a hard disk drive is used as the external device 3b and the external device 3b and the display device 4 is connected with a wire or a without a wire for the data transmission and the data reception therebetween.

Next, the capsule endoscope 2 and the receiving apparatus 3 are described. According to the first embodiment, the capsule endoscope 2 is for functioning as a transmitting apparatus and a body insertable apparatus within a scope of claims, and includes a function for acquiring image information of the body cavity image and transmitting the radio signal to the receiving apparatus 3 by being inserted into the subject 1.

Figure 2:
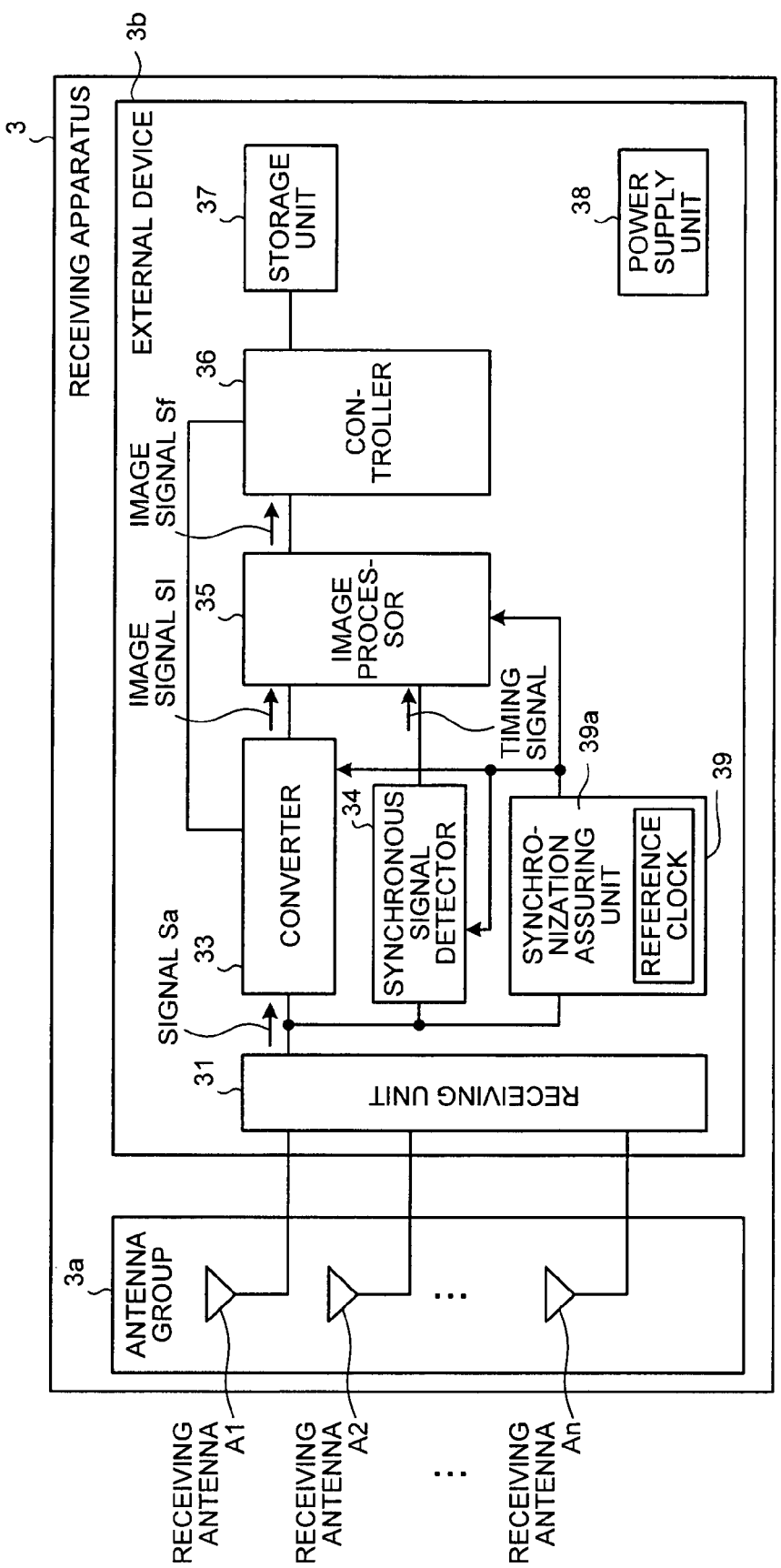
FIG. 2 is a block diagram of a configuration of a receiving apparatus shown in FIG. 1.

The receiving apparatus 3 is firstly described. FIG. 2 is a block diagram for describing an entire configuration of the receiving apparatus 3. As shown in FIG. 1 and FIG. 2, the receiving apparatus 3 has a configuration to include the antenna group 3a that includes receiving antennas Al to An for receiving the radio signal transmitted from the capsule endoscope 2, and the external device 3b that performs a predetermined process for the radio signal received via the receiving antennas Al to An.

The receiving antennas Al to An are for receiving the radio signal transmitted from the capsule endoscope 2. More specifically, each of the receiving antennas Al to An has a configuration to include a loop antenna and a fixing unit for fixing the loop antenna on the surface of the subject 1. According to the first embodiment, because the capsule endoscope 2 as a radio signal transmission source is to be inserted into the subject 1 and performs a radio signal transmission while the capsule endoscope 2 travels inside the subject 1, the receiving antennas Al to An have such a configuration that one antenna is selected from the receiving antennas Al to An so that a receiving condition of the radio signal becomes most optimal, for example, a receiving strength becomes maximum depending on a position of the capsule endoscope 2, based on a control by the external device 3b, and a reception of the radio signal is performed via a selected receiving antenna A.

The external device 3b is for performing a predetermined receiving process for the radio signal received via any one of the receiving antennas Al to An. The external device 3b includes, as shown in FIG. 2, a receiving unit 31, a converter 33, a synchronous signal detector 34, an image processor 35, a controller 36, a storage unit 37, and a power supply unit 38. The receiving unit 31 switches the antenna A used for receiving the radio signal, performs the receiving process such as a demodulation, analogue/digital conversion for the radio signal received via the switched antenna A, and outputs a signal Sa. The converter 33 converts the signal Sa output from the receiving unit 31 into an image signal Sl in a signal format processable by the image processor 35. For example, when the signal Sa is in a serial format, the converter 33 outputs the image signal Sl converted into a parallel format. The synchronous signal detector 34 detects various synchronous signals from the signal Sa, and outputs a timing signal St that instructs a timing of an image process in the image processor 35. The image processor 35 performs a predetermined process for the image signal Sl output from the converter 33, and outputs an image signal Sf corresponding to an image of one frame. The controller 36 performs an entire control and an output control for the image signal Sf input via the image processor 35. A synchronization assuring unit 39 includes a reference clock 39a that outputs a clock signal that is to be a process reference for the radio signal transmitted from the capsule endoscope 2. When a predetermined reference signal component is included in the radio signal received by the receiving unit 31, the synchronization assuring unit 39 changes a frequency of the clock signal of the reference clock 39a in response to a frequency variation of the radio signal transmitted from the capsule endoscope 2, by using a reference signal included in the reference signal component, and synchronizes the frequency between the radio signal transmitted from the capsule endoscope 2 and the reference clock 39a. The storage unit 37 stores the image signal Sf based on a control by the controller 36. Each of the images captured by the capsule endoscope 2 is stored in the storage unit 37. The power supply unit 38 supplies driving power for each of the above components. The external device 3b instructs the receiving unit 31 to detect the strength of the radio signal received via the receiving antenna A and to cause the controller 36 to switch the antenna A used for receiving the radio signal to the antenna A with the maximum receiving strength.

Figure 3:
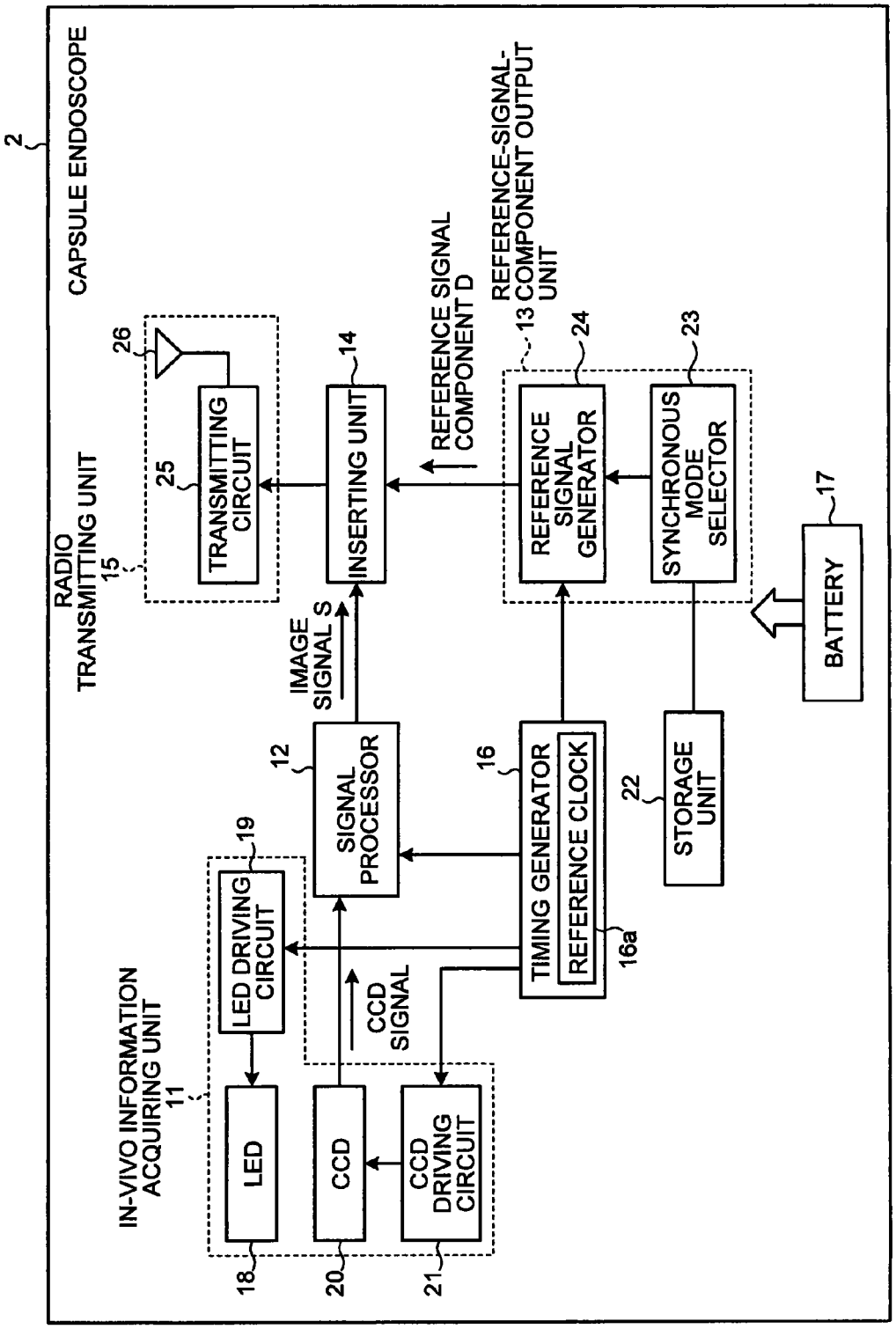
FIG. 3 is a block diagram of a configuration of a capsule endoscope shown in FIG. 1.

Next, the capsule endoscope 2 is described. FIG. 3 is a block diagram for describing a schematic configuration of the capsule endoscope 2. As shown in FIG. 3, the capsule endoscope 2 includes an in-vivo information acquiring unit 11 for acquiring in-vivo information as a process target in a signal processor 12, and a radio transmitting unit 15 for wirelessly transmitting the acquired in-vivo information to the receiving apparatus 3. The capsule endoscope 2 includes the signal processor 12 that performs a predetermined process for the in-vivo information output from the in-vivo information acquiring unit 11 (the in-vivo information is described as a CCD signal C in the first embodiment) and that outputs the signal image S.

The capsule endoscope 2 includes a reference-signal-component output unit 13 that generates and outputs a reference signal component D with the frequency selected in response to a synchronous mode in the capsule endoscope 2. The reference signal component D is used for synchronizing the reference clock 39a of the receiving apparatus 3 with the radio signal transmitted from the capsule endoscope 2, and includes at least the reference signal that includes different signal levels.

The capsule endoscope 2 includes an inserting unit 14 that inputs the reference signal component D into the image signal S output from the signal processor 12 and outputs the signal to the radio transmitting unit 15, when the reference signal component D is output from the reference-signal-component output unit 13. The inserting unit 14 inserts the reference signal component D output from the reference-signal-component output unit 13 into a predetermined heading period or a horizontal blanking period in which a signal component does not exist, for the image signal S, and outputs the signal. In some cases, the inserting unit 14 includes a function for superimposing the reference signal component D on the predetermined signal component as well as for inserting the reference signal component D.

The capsule endoscope 2 further includes a timing generator 16 for synchronizing a driving timing of each of the above components. The timing generator 16 includes a reference clock 16a that outputs a clock signal with a frequency of, i.e., x[MHz], and controls the driving timing of each of the components by using the clock signal output from the reference clock 16a.

The capsule endoscope 2 includes a battery 17 for supplying the driving power of each of the components, and a storage unit 22 that stores instruction information for instructing a synchronous mode in the capsule endoscope 2, that is, for instructing whether the reference signal component is inserted and the frequency of the reference signal included in the reference signal component to be inserted. The storage unit 22 stores identification information such as a use, a type, or a product number, and the identification information functions as the instruction information.

The in-vivo information acquiring unit 11 is for acquiring the in-vivo information when the capsule endoscope 2 is inserted into the subject 1. According to the first embodiment, the body cavity image is acquired as the in-vivo information, and the in-vivo information acquiring unit 11 has a configuration to include an imaging function for acquiring an image. More specifically, the in-vivo information acquiring unit 11 includes a light emitting diode (LED) 18 that functions as an illuminating unit, an LED driving circuit 19 that controls a drive of the LED 18, a charge coupled device (CCD) 20 that functions as the imaging unit for capturing an image of at least a portion of an area illuminated by the LED 18 and outputs the CCD signal C as the image information, and a CCD driving circuit 21 that controls a drive of the CCD 20. Each of the LED driving circuit 19 and the CCD driving circuit 21 controls each of the drive of the LED 18 and the CCD 20 based on a timing instructed by the timing generator 16. Although the CCD is used as the imaging unit according to the first embodiment, this configuration is not necessary, and the imaging unit can be configured by, for example, a complementary metal-oxide semiconductor (CMOS).

The radio transmitting unit 15 is for wirelessly transmitting information input via the inserting unit 14 to an outside. More specifically, the radio transmitting unit 15 has a configuration to include a transmitting circuit 25 that performs a necessary modulation process for the input information, and a transmitting antenna 26.

The signal processor 12 is for generating the image signal S by performing a predetermined process for the CCD signal C acquired by the CCD 20, and functions as an information main-frame output unit within a scope of claims. The image signal S output by the signal processor 12 functions as a main frame portion of information within a scope of claims. The signal processor 12 outputs a scan line component Se corresponding to each of scan lines of the image information captured by the CCD 20, in a image signal period TM that structures one frame period (frame cycle) corresponding to one image. The image signal S includes a heading synchronization period TS including a heading standard synchronization component Sd that includes a vertical synchronous signal, and the image signal period TM having a structure in which the scan line component Se corresponding to each of the scan lines that includes a horizontal synchronous signal is provided and a horizontal blanking period Th as a predetermined blanking period is also provided between each of the scan line components Se. Any signal components are not included in the horizontal blanking period Th. The vertical synchronous signal and the horizontal synchronous signal are signals used for restructuring an image in the receiving apparatus 3, and the horizontal synchronous signal is used for synchronizing in a vertical direction while the horizontal synchronous signal is used for synchronizing in a horizontal direction.

The reference-signal-component output unit 13 is for selecting the synchronous mode in the capsule endoscope 2 corresponding to the receiving apparatus 3 based on the instruction information stored in the storage unit 22, generating the reference signal with the frequency corresponding to the selected synchronous mode, and outputting the reference signal component D including the generated reference signal according to a timing instructed by the timing generator 16. The reference-signal-component output unit 13 includes a synchronous mode selector 23 and a reference signal generator 24. The synchronous mode selector 23 selects the synchronous mode in the capsule endoscope 2 based on the instruction information stored in the storage unit 22. More specifically, the synchronous mode selector 23 selects whether the reference signal component corresponding to the synchronous mode in the capsule endoscope 2 is inserted, and selects the frequency of the reference signal included in the reference signal component for inserting the reference signal component. The synchronous mode selector 23 selects one mode from among a complete synchronous mode in which a frequency corresponding to the frequency of the image signal S output by the signal processor 12 is used as the reference signal, a fixed synchronous mode in which a frequency corresponding to the frequency of the CCD signal C output by the in-vivo information acquiring unit 11 is used as the reference signal, and an asynchronous mode in which the reference signal is not used and the reference signal component is not inserted. The reference signal generator 24 generates the reference signal with the frequency corresponding to the synchronous mode selected by the synchronous mode selector 23 and outputs the reference signal component D including the generated reference signal. When the complete synchronous mode is selected by the synchronous mode selector 23, the reference signal generator 24 generates a complete reference signal with the frequency corresponding to the frequency of the image signal S output by the signal processor 12, and outputs a complete-reference-signal component Dp including the complete reference signal. When the fixed synchronous mode is selected by the synchronous mode selector 23, the reference signal generator 24 generates a fixed reference signal with the frequency corresponding to the frequency of the CCD signal C output by the in-vivo information acquiring unit 11, and outputs a fixed-reference-signal component Dc including the fixed reference signal. When the asynchronous mode is selected by the synchronous mode selector 23, the reference signal generator 24 does not generate a signal.

At this state, if the frequency of the reference clock 16a in the capsule endoscope 2 is determined as x[MHz], an output frequency of the image signal S output by the signal processor 12 is (x/6) [MHz]. The frequency of the driving clock of the CCD 20 is (x/4)[MHz] by a frequency dividing of the reference clock x[MHz]. The timing generator 16 includes a supply source that supplies a signal with the (x/6) [MHz] frequency of the image signal S, and a supply source that supplies a signal with the (x/4) [MHz] frequency of the driving clock of the CCD 20, and controls a process timing for each of the components based on the signal output from the supply sources.

The reference signal generator 24 generates and outputs a signal with a frequency of (½") of (x/6)[MHz], as the complete reference signal. Further, the reference signal generator 24 generates and outputs a signal with a frequency of (½") of (x/4) [MHz], as the fixed reference signal. For example, the reference signal generator 24 includes a complete-change frequency dividing circuit that divides a signal having the (x/6)[MHz] frequency and a fixed-change frequency dividing circuit that divides a signal having the (x/4)[MHz] frequency. The supply sources for each of the frequency dividing circuits and for each of the signals in the reference signal generator 24 are provided via a switch.

When selecting the complete synchronous mode, the synchronous mode selector 23 changes the switch between the complete-change frequency dividing circuit and the power source of the (x/6)[MHz] signal to be in an ON state to enable to supply the (x/6)[MHz] signal to the reference signal generator 24. As a result, the reference signal generator 24 can generate and output the complete reference signal. When selecting the fixed synchronous mode, the synchronous mode selector 23 changes the switch between the fixed-change dividing circuit and the power source of the (x/4)[MHz] signal to be in an ON state to enable to supply the (x/4)[MHz] signal to the reference signal generator 24. As a result, the reference signal generator 24 can generate and output the fixed reference signal. When selecting the asynchronous mode, the synchronous mode selector 23 keeps an OFF state for every switch to stop supplying the signal to the reference signal generator 24. Accordingly, the reference signal generator 24 does not generate any signals.

Figure 4:
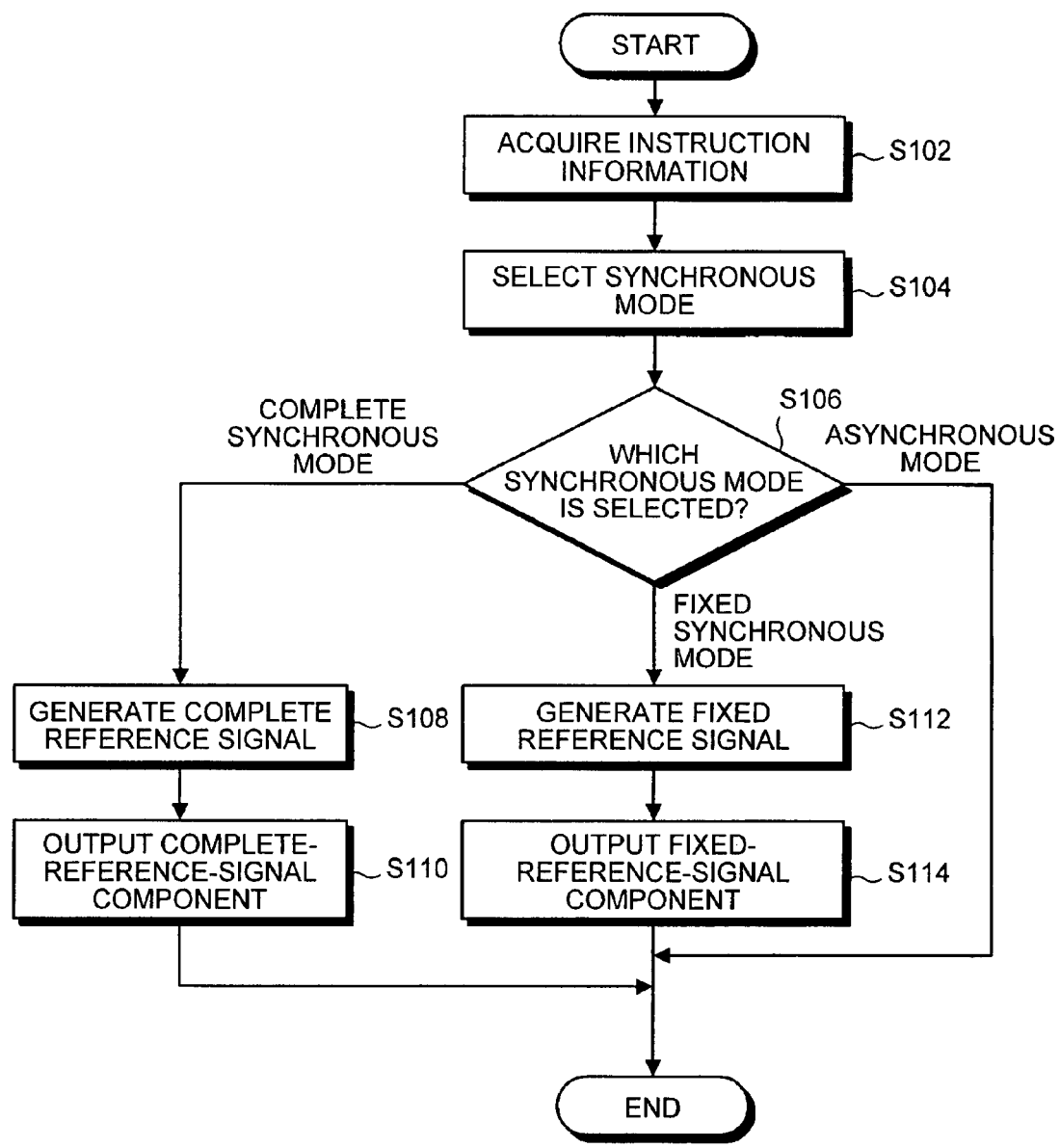
FIG. 4 is a flowchart for describing a process operation of a reference-signal-component output unit shown in FIG. 3.

Next, a process operation of the reference-signal-component output unit 13 is described with reference to FIG. 4. FIG. 4 is a flowchart for describing the process operation of the reference-signal-component output unit 13 shown in FIG. 3. As shown in FIG. 4, the synchronous mode selector 23 acquires the instruction information and the like stored in the storage unit 22 (step S102), and selects one synchronous mode from the complete synchronous mode, the fixed synchronous mode, and the asynchronous mode, based on the acquired instruction information (step S104). Thereafter, the reference signal generator 24 determines that the synchronous mode selected by the synchronous mode selector 23 is whether the complete synchronous mode, the fixed synchronous mode, or the asynchronous mode (step S106). When determining that the synchronous mode selected by the synchronous mode selector 23 is the complete synchronous mode (step S106: complete synchronous mode), the reference signal generator 24 generates the complete reference signal (step S108), and outputs the complete-reference-signal component Dp including the generated complete reference signal to the inserting unit 14 in accordance with a process timing instructed by the timing generator 16 (step S110). When determining that the synchronous mode selected by the synchronous mode selector 23 is the fixed synchronous mode (step S106: fixed synchronous mode), the reference signal generator 24 generates the fixed reference signal (step S112), and outputs the fixed-reference-signal component Dc including the generated fixed reference signal to the inserting unit 14 in accordance with the process timing instructed by the timing generator 16 (step S114). When determining that the synchronous mode selected by the synchronous mode selector 23 is the asynchronous mode (step S106: asynchronous mode), the reference signal generator 24 does not generate and output the reference signal.

Next, the complete synchronous mode is described. For example, when the synchronous mode selector 23 acquires information indicating that the capsule endoscope 2 is for an esophageal region for which an imaging period is short from among the identification information stored in the storage unit 22, the synchronous mode selector 23 selects the complete synchronous mode.

Figure 5:
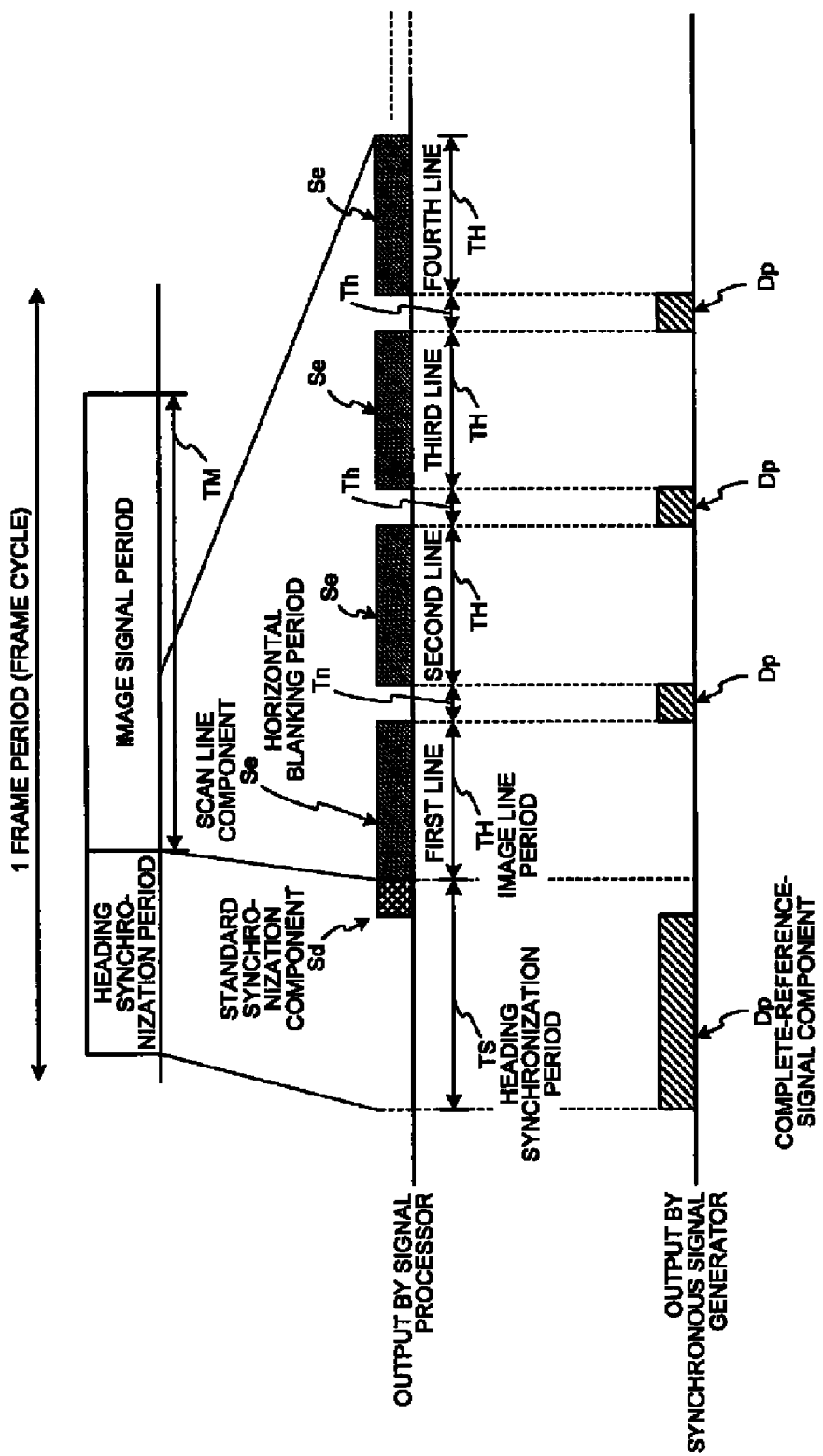
FIG. 5 is a schematic view for describing a signal component output from the reference-signal-component output unit and a signal processor shown in FIG. 3.

At this state, the signal processor 12 outputs the image information captured by the CCD 20 in the image signal period TM that structures one frame period (frame cycle) corresponding to one image. More specifically, as shown in FIG. 5, image periods TH corresponding to number of the scan lines are provided in the image signal period TM, and the signal processor 12 generates and outputs the scan line component Se corresponding to each of the scan lines with respect to each image line period TH. The signal processor 12 generates the horizontal synchronous signal and outputs the horizontal synchronous signal added to the heading portion of the scan line component Se. The horizontal blanking period Th is provided between each of the adjacent image line periods TH, and any signals are not included in the horizontal blanking period Th of the image signal S output from the signal processor 12. At the heading portion of the one frame period, a heading synchronization period corresponding to a process preparation period for the one image on the side of the receiving apparatus, and the signal processor 12 generates the vertical synchronization signal in the heading synchronization period TS, and outputs the standard synchronization component Sd including the vertical synchronization signal. The image signal S is configured to include the standard synchronization component Sd, each of the scan line components Se, and the horizontal blanking period Th between each of the scan line components Se.

When the complete synchronous mode is selected by the synchronous mode selector 23, the reference signal generator 24 generates the complete reference signal and outputs the complete-reference-signal component Dp. As shown in FIG. 5, the reference-signal-component output unit 13 outputs the complete-reference-signal component Dp in response to a first half period of the heading synchronization period TS and to the horizontal blanking period Th, under a control of the timing generator 16. Further, as described above, the signal processor 12 outputs the standard synchronization component Sd in the heading synchronization period TS and outputs the scan line component Se in each of the image line periods TH, under a control of the timing generator 16. As described, when the complete synchronous mode is selected by the synchronous mode selector 23, the timing generator 16 determines the output timing of the complete-reference-signal component Dp in the reference signal generator 24 to be corresponding to the first half period of the heading synchronization period TS and with the horizontal blanking period Th.

Figure 6:
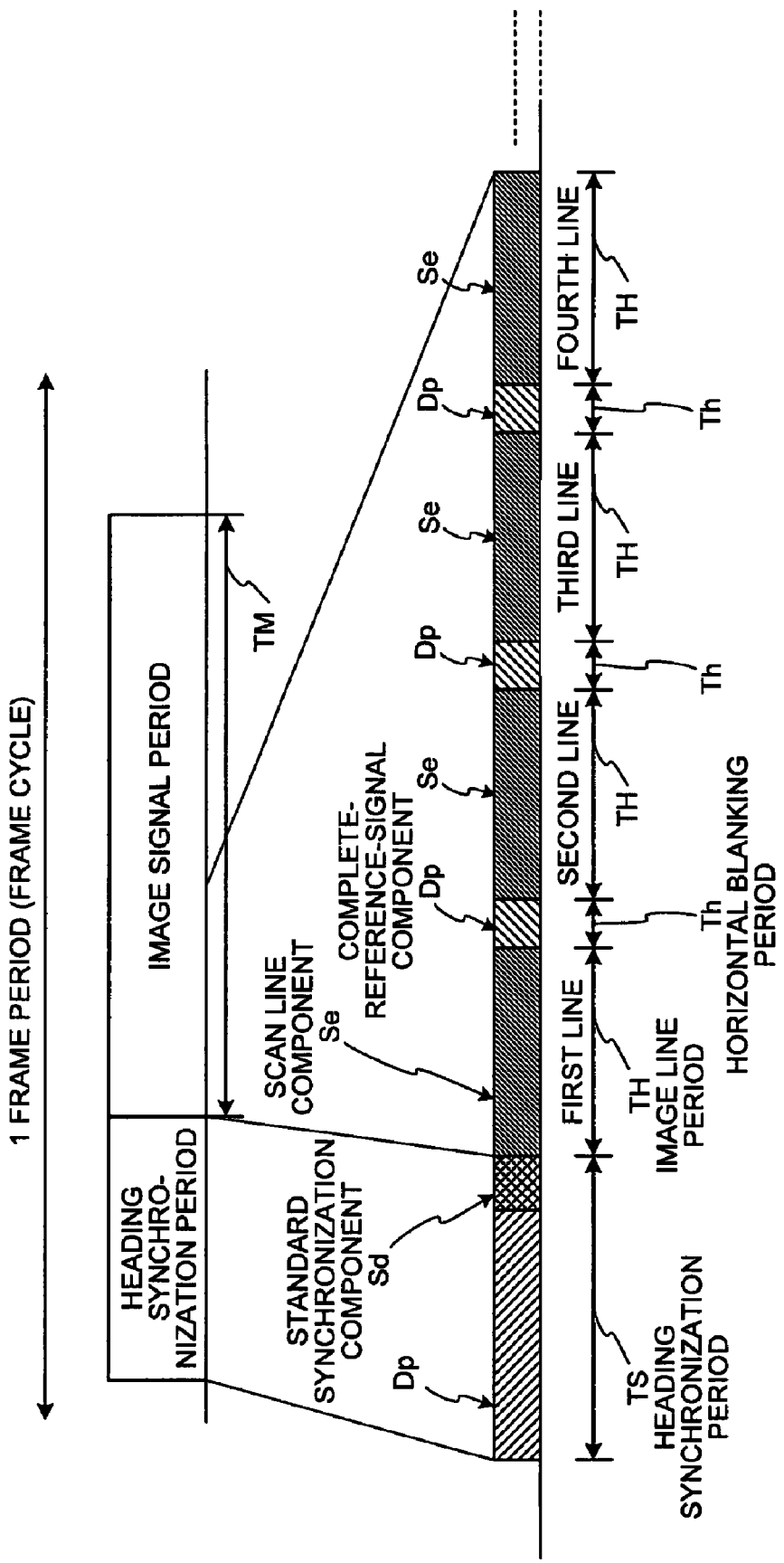
FIG. 6 is a schematic view for describing a signal component output from an inserting unit shown in FIG. 3.

As a result, as shown in FIG. 6, the configuration of the signal output from the inserting unit 14 is such that the complete-reference-signal component Dp is inserted into the first half period of the heading synchronization period TS, and the complete-reference-signal component Dp is inserted into the horizontal blanking period Th between each of the scan line components Se. In other words, the capsule endoscope 2 transmits the radio signal including the image information from the radio transmitting unit 15 to the receiving apparatus 3, in such a state that the complete-reference-signal component Dp is inserted into the first half period of the heading synchronization period TS and to the horizontal blanking period Th.

On the side of the receiving apparatus 3, the complete reference signal is extracted from the complete-reference-signal component Dp inserted in the first half period of the heading synchronization period TS and the horizontal blanking period Th, from the received radio signal. The receiving apparatus 3 performs a phase comparison between the extracted complete reference signal and the signal divided from the clock signal output from the reference clock 39a on the side of the receiving apparatus 3, to assure synchronization between the frequency of the signal divided from the clock signal output from the reference clock 39a on the side of the receiving apparatus 3 and the radio signal transmitted from the capsule endoscope 2. Thereafter, the receiving apparatus 3 repeats the process for assuring the synchronization between the side of the receiving apparatus and the radio signal transmitted from the capsule endoscope 2 with respect to each period corresponding to the horizontal blanking period Th, by using the complete reference signal of the complete-reference-signal component Dp inserted in the horizontal blanking period Th, to synchronize the frequency of the reference clock 39a in response to the variation of the radio signal transmitted from the capsule endoscope 2. Accordingly, because the receiving apparatus 3 can completely synchronize the frequency of the reference clock 39a with the frequency of the radio signal transmitted from the capsule endoscope 2, even when the vertical synchronous signal and the horizontal synchronous signal are not accurately detected from the radio signal transmitted from the capsule endoscope 2, it becomes possible to accurately acquire the image captured by the capsule endoscope 2.

Figure 7:
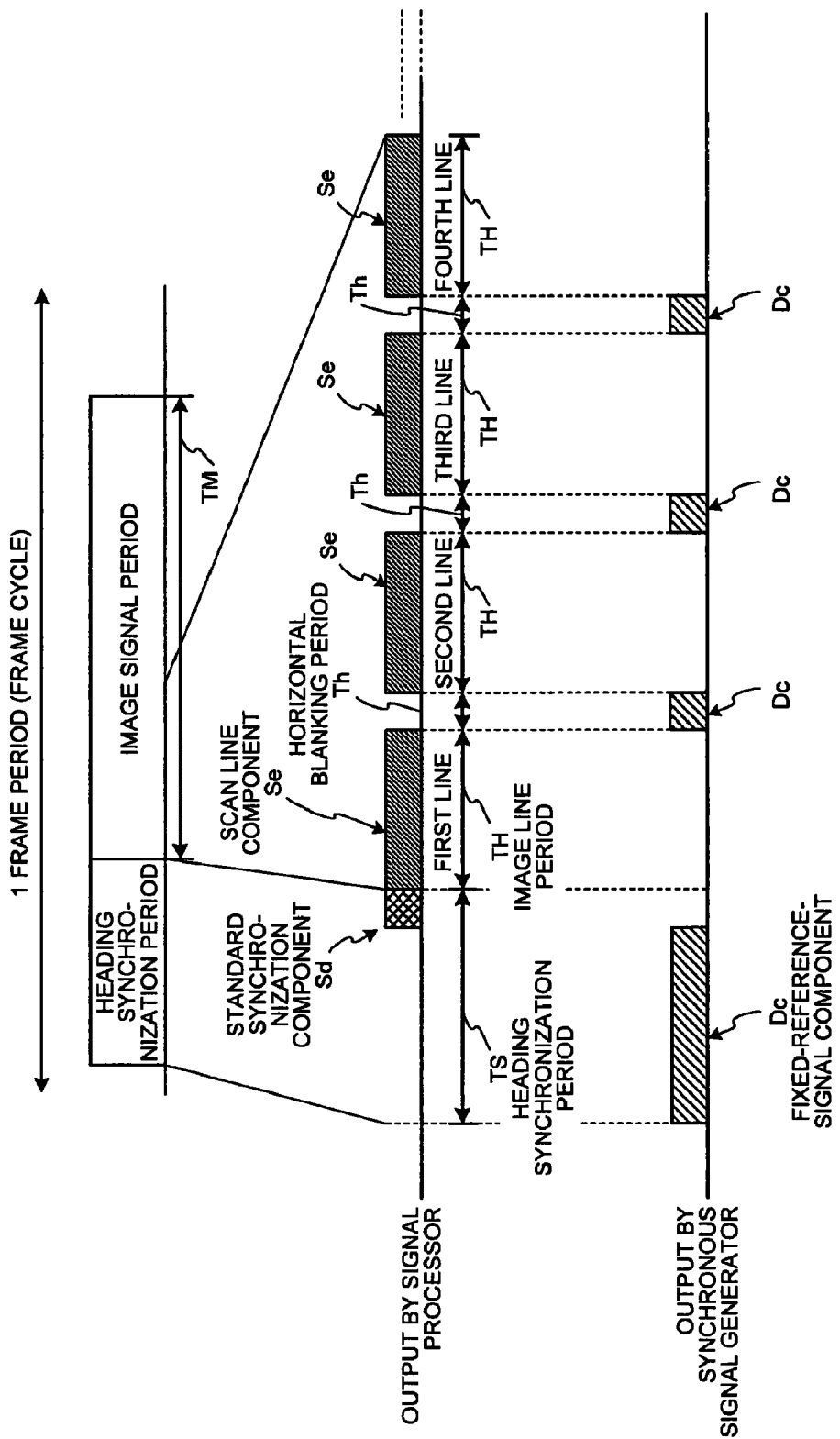
FIG. 7 is a schematic view for describing a signal component output from the reference-signal-component output unit and the signal processor shown in FIG. 3.

Next, the fixed synchronous mode is described. For example, when the synchronous mode selector 23 acquires such information, from among the identification information stored in the storage unit 22, that indicates that the capsule endoscope 2 is for the esophageal region for which the imaging period is short and in a type with which noise is mixed into the image information captured by the CCD 20, the synchronous mode selector 23 selects the fixed synchronous mode. In this case, the reference signal generator 24 generates a fixed-reference-signal corresponding to the output frequency (x/4) [MHz] of the CCD signal C, and outputs a fixed-reference-signal component Dc including the fixed-reference-signal. As shown in FIG. 7, the reference-signal-component output unit 13 outputs the fixed-reference-signal component Dc including the fixed reference signal in response to the first half period of the heading synchronization period TS and to the horizontal blanking period Th. In this case, when the fixed synchronous mode is selected by the synchronous mode selector 23, the timing generator 16 determines the output timing of the fixed-reference-signal component Dc in the reference signal generator 24 to be corresponding to the timing of the first half period of the heading synchronization period TS and the horizontal blanking period Th.

Figure 8:
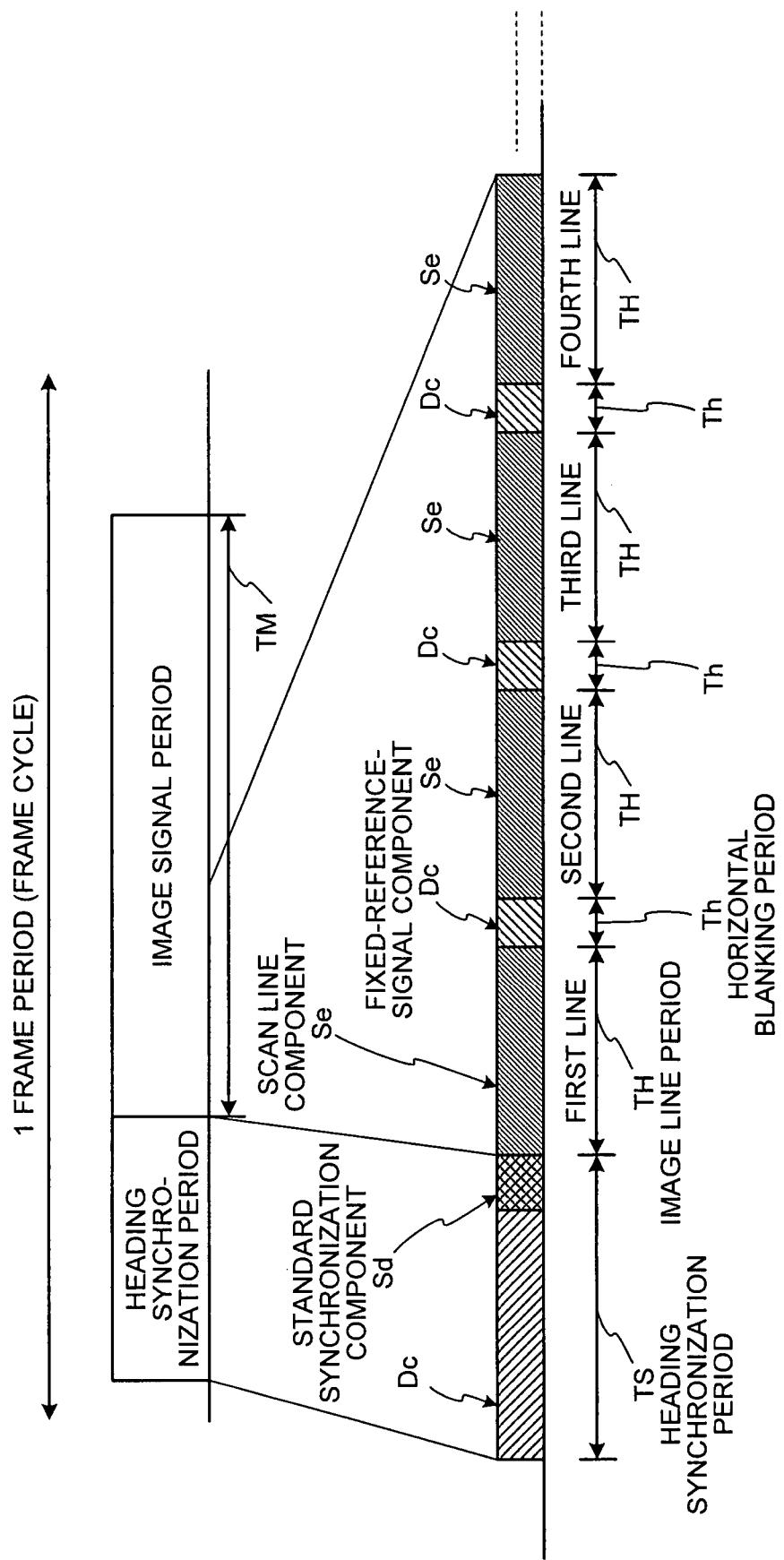
FIG. 8 is a schematic view for describing a signal component output from the inserting unit shown in FIG. 3.

As a result, as shown in FIG. 8, the configuration of the signal output from the insertion unit 14 is such that the fixed-reference-signal component Dc is inserted into the first half period of the heading synchronization period TS and the fixed-reference-signal component Dc is inserted into the horizontal blanking period Th between each of the scan line components Se. In other words, the capsule endoscope 2 transmits the radio signal including the image information from the radio transmitting unit 15 to the receiving apparatus 3, in such a state that the fixed reference signal is inserted in the first half period of the heading synchronization period TS and in the horizontal blanking period Th.

On the side of the receiving apparatus 3, the fixed-reference-signal is extracted from the fixed-reference-signal component Dc in the heading synchronization period TS, from the received radio signal, and the frequency of the clock signal in the reference clock 39a of the receiving apparatus 3 is adjusted and synchronized with the frequency variation of the radio signal, by using the fixed reference signal. The vertical synchronous signal is extracted from the signal component in the heading synchronization period TS and the heading portion of the image signal of one frame is detected. Thereafter, the controller 36 repeats to change the frequency of the clock signal of the reference clock 39a in response to the frequency variation of the radio signal transmitted from the capsule endoscope 2, by using the fixed reference signal of the fixed-reference-signal component Dc inserted in the horizontal blanking period Th, and keeps the synchronization between the frequency of the radio signal and the frequency of the clock signal of the reference clock 39a. As a result, because the receiving apparatus 3 enables to accurately detect the heading portion of each of the scan lines by using the fixed reference signal inserted in the horizontal blanking period Th, and to detect the heading portion of the image information corresponding to each of the scan lines, it becomes possible to accurately acquire the image information corresponding to an entire one image.

Figure 9:
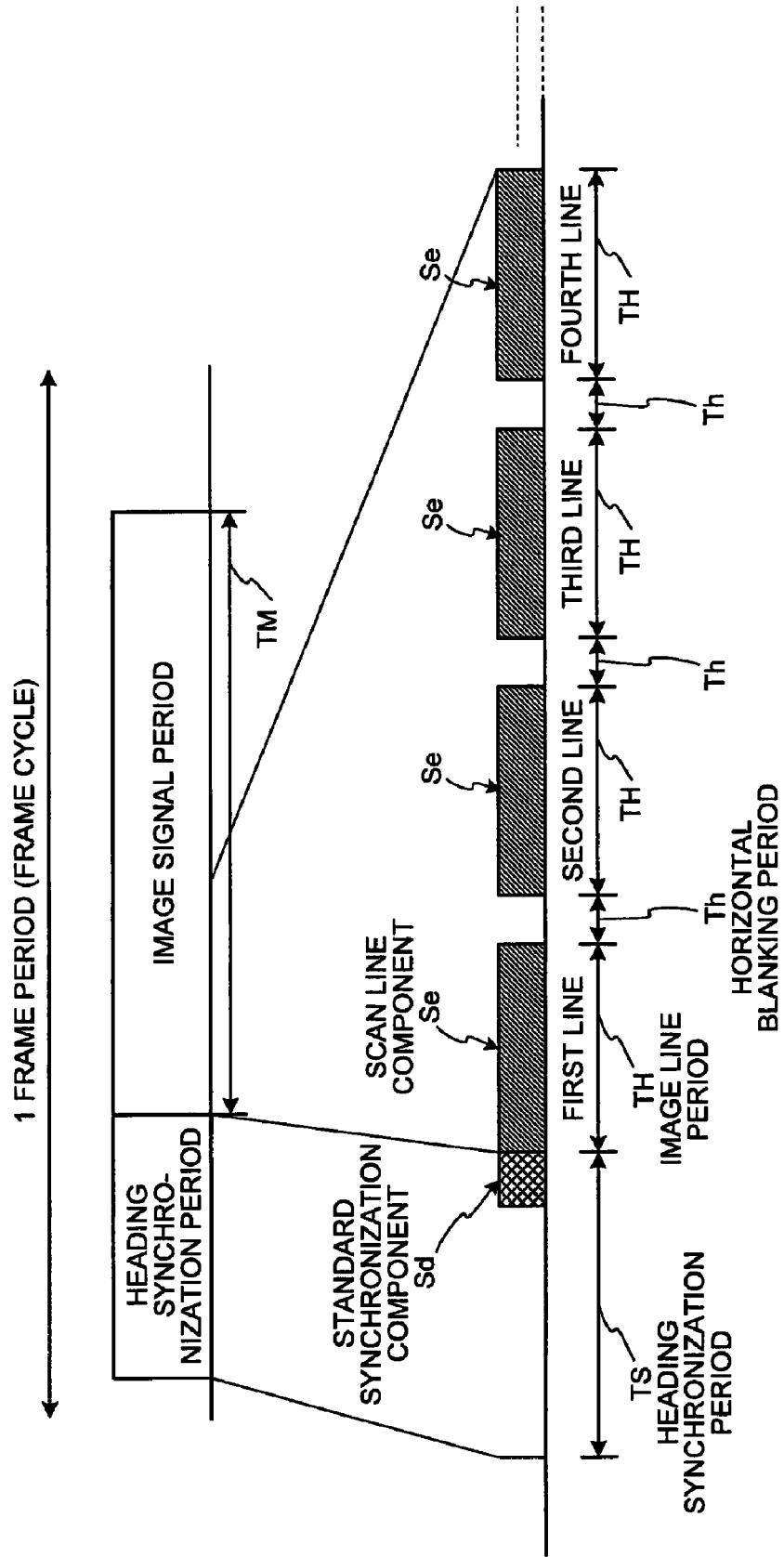
FIG. 9 is a schematic view for describing a signal component output from the inserting unit shown in FIG. 3.

Next, the asynchronous mode is described. When the synchronous mode selector 23 acquires such information, from among the identification information stored in the storage unit 22, that indicates that the capsule endoscope 2 is for the small intestine for which the imaging period is long, the synchronous mode selector 23 does not select to insert the reference signal component D, and the reference signal generator 24 does not generate and output the reference signal component to be inserted into the heading synchronization period TS and the horizontal blanking period Th. As a result, as shown in FIG. 9, the signal output from the inserting unit 14 is configured by the standard synchronization component Sd in the heading synchronization period TS and the scan line component Se in the image line period TH. In this case, the receiving apparatus 3 extracts the vertical signal and the horizontal signal from the received radio signal, and processes the image signal included in the radio signal received by using the vertical signal and the horizontal signal. When the capsule endoscope 2 transmits the radio signal by using the asynchronous mode, it is not required to generate the reference signal to be inserted into the horizontal blanking period Th. Therefore, when the asynchronous mode is selected, it becomes possible to reduce the power consumption in the capsule endoscope 2 compared to the cases in which the complete synchronous mode and the fixed synchronous mode are selected. Specifically, the asynchronous mode is suitable when the capsule endoscope 2 captures images and transmits the image information for a long time.

As described, the capsule endoscope 2 according to the first embodiment enables to select a plurality of the synchronous modes including not only the asynchronous mode but also the complete synchronous mode and the fixed synchronous mode that can change the frequency of the reference clock at the reception side in response to the frequency variation of the radio signal transmitted from the reception side, and to flexibly select the proper synchronous mode. Further, with the capsule endoscope 2 according to the first embodiment, the complete synchronous mode or the fixed synchronous mode is selected depending on a use, and the signal in which the reference signal component D including the complete reference signal or the fixed reference signal is inserted is transmitted. By using the reference signals, it becomes possible to, in the receiving apparatus 3, change the frequency of the reference clock 39a in response to the frequency variation of the transmission signal transmitted from the capsule endoscope 2, to synchronize the frequency of the radio signal transmitted from the capsule endoscope 2 with the frequency of the reference clock of the receiving apparatus, and to accurately process the received radio signal regardless of the frequency variation. Therefore, even when the vertical synchronous signal and the horizontal synchronous signal are not accurately detected, the receiving apparatus 3 can accurately process the image information. As a result, the receiving apparatus 3 can provide the accurate body cavity image acquired by the capsule endoscope 2 to a user and support an accurate examination made by the user.

It is acceptable that the synchronous mode selector 23 changes the synchronous mode in the capsule endoscope 2 at a predetermined timing, based on the instruction information and the like stored in the storage unit 22. For example, the synchronous mode selector 23 selects the complete synchronous mode or the fixed synchronous mode for a period corresponding to the esophageal region for which the imaging period is short, while the synchronous mode selector 23 selects the asynchronous mode for a period corresponding to the small intestine for which the imaging period is long. As described, it is acceptable to change the most suitable synchronous mode for an imaged region during the operation of the capsule endoscope 2. Further, according to the first embodiment, it is described that the synchronous mode selector 23 selects the synchronous mode based on the instruction information stored in the storage unit 22, however, it is not thus limited. For example, if the capsule endoscope 2 includes the receiving function, the synchronous mode selector 23 can select the synchronous mode based on the instruction information transmitted from an outside.

(Second Embodiment)

Next, a second embodiment is described. According to the second embodiment, in a receiving apparatus that processes a radio signal transmitted from the capsule endoscope by using the asynchronous mode, a predetermined reproduction signal is generated for a scan line for which the horizontal synchronous signal is not detected, and an image signal is processed based on the generated reproduction signal.

Figure 10:
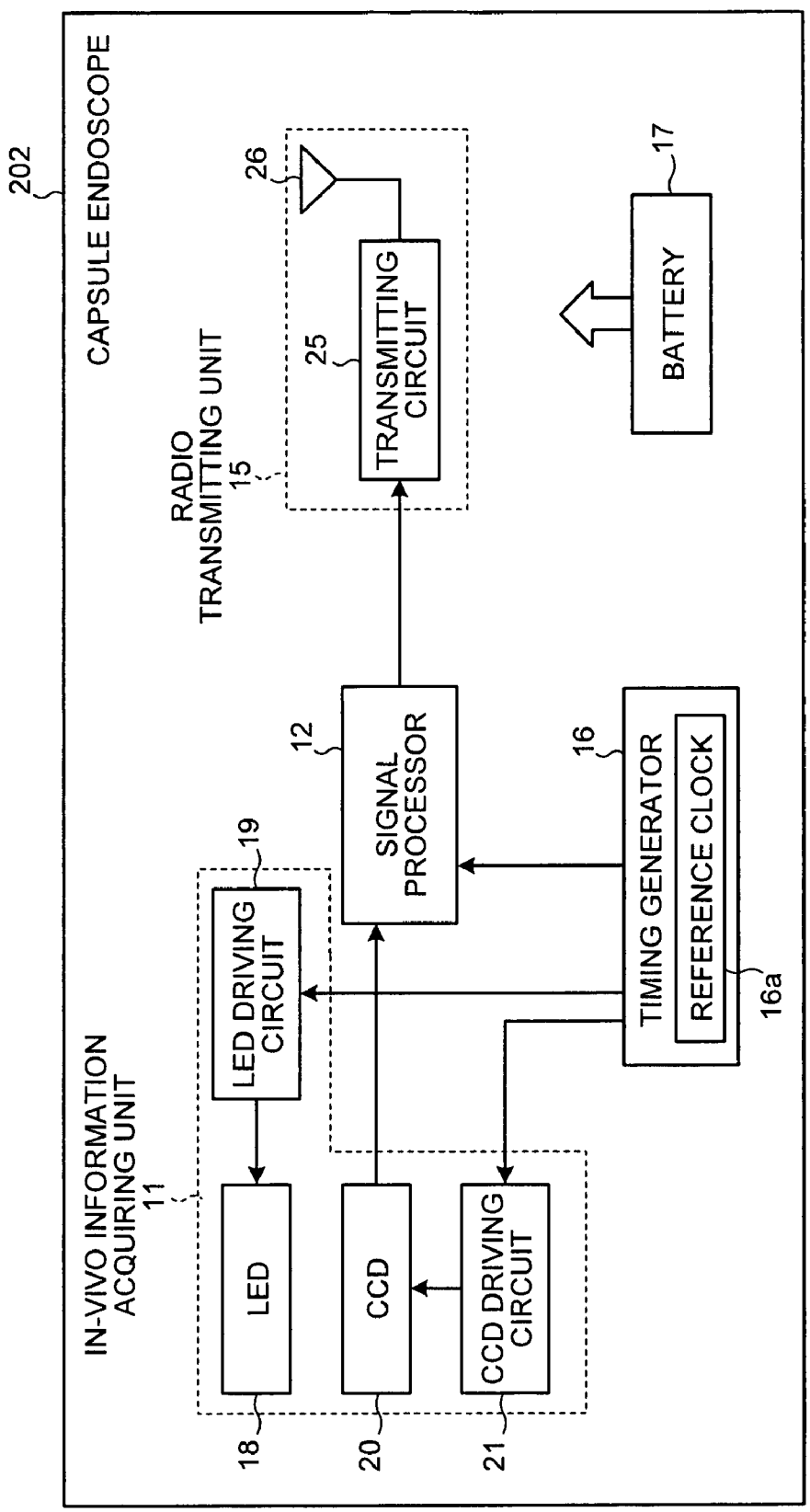
FIG. 10 is a block diagram of a configuration of a capsule endoscope according to a second embodiment of the present invention.

FIG. 10 is a block diagram for exemplifying a schematic configuration of a capsule endoscope according to the second embodiment. The capsule endoscope according to the second embodiment has such a configuration, for example, like a capsule endoscope 202 shown in FIG. 10, that the reference-signal-component output unit 13, the inserting unit 14, and the storage unit 22 are excluded compared to the capsule endoscope 2 shown in FIG. 3, and transmits the radio signal by using the above described asynchronous mode. Accordingly, from the capsule endoscope 202, as shown in FIG. 9, such a radio signal is transmitted that corresponds to the image signal S having a configuration to include the heading synchronization period TS including the vertical synchronous signal, and the image signal period TM including, one after the other, the image line period TH in which the scan line component SE including the horizontal synchronous signal is transmitted and the horizontal blanking period Th.

Figure 11:
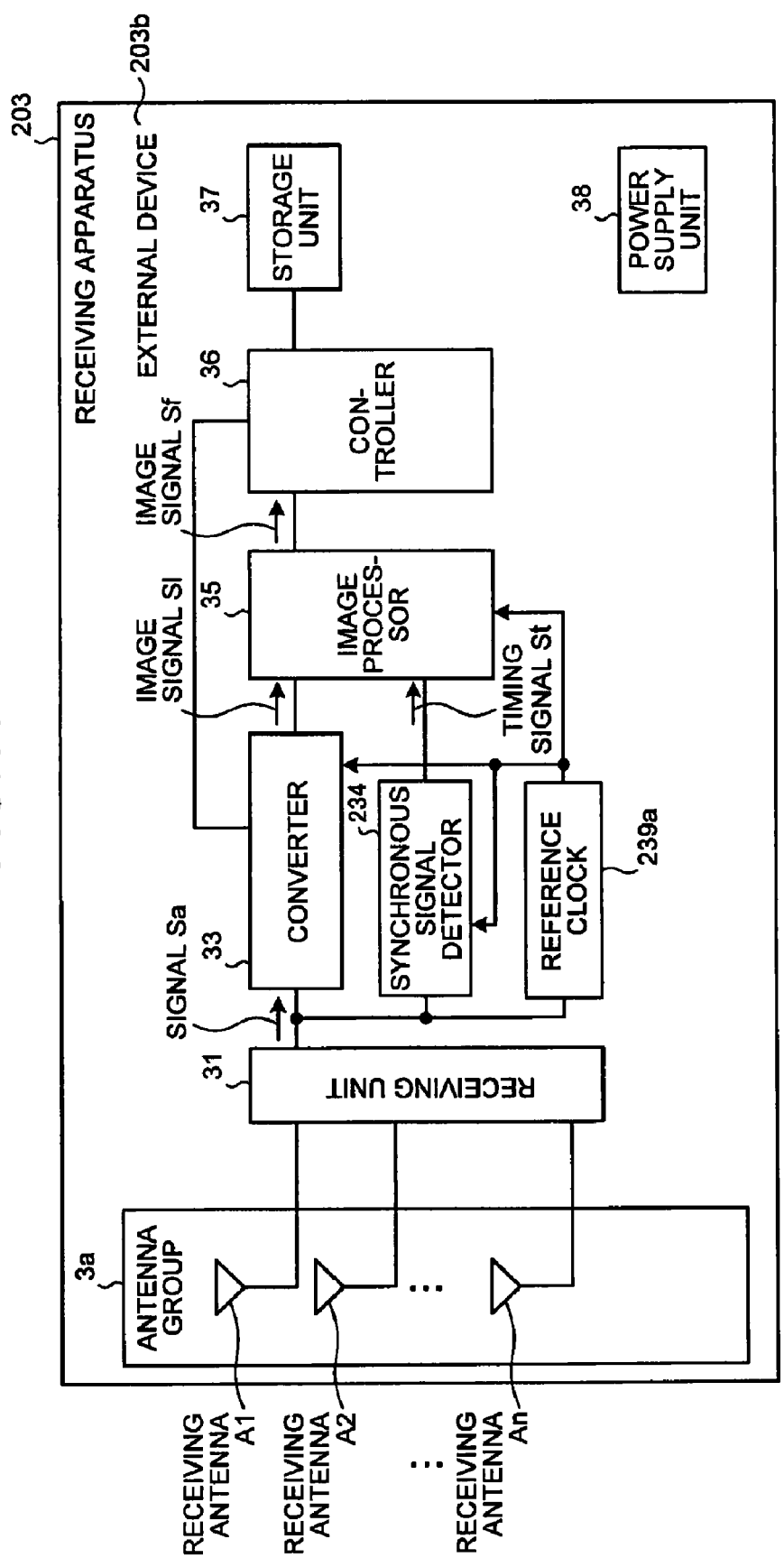
FIG. 11 is a block diagram of a configuration of a receiving apparatus according to the second embodiment.

Next, a receiving apparatus according to the second embodiment is described. FIG. 11 is a block diagram for describing a schematic configuration of the receiving apparatus according to the second embodiment. As shown in FIG. 11, a receiving apparatus 203 according to the second embodiment includes a reference clock 239a that includes the same function of the reference clock 39a, instead of the reference clock 39a, compared to the receiving apparatus 3 shown in FIG. 2. The receiving apparatus 203 further includes an external device 203b having a synchronous signal detector 234, instead of the synchronous signal detector 34. The synchronous signal detector 234 detects the vertical synchronous signal and the horizontal synchronous signal from the signal Sa output from the receiving unit 31, based on a clock signal output from the reference clock 239a, and outputs to the image processor 35, a timing signal for instructing a timing of a process operation in the image processor 35 based on the vertical synchronous signal and the horizontal synchronous signal. When the horizontal synchronous signal is not detected, the synchronous signal detector 234 generates the reproduction signal for the corresponding scan line, and outputs the timing signal St to the image processor 35, based on the generated reproduction signal. The image processor 35 starts to process an image signal Sl by synchronizing with an input timing of the image signal Sl based on the timing signal output from the synchronous signal detector 234. More specifically, the image processor 35 separates a pixel signal corresponding to a heading pixel of one frame and to the heading pixel of each of the scan lines, and performs a predetermined process for every pixel signal, based on the timing signal output from the synchronous signal detector 234. At this sate, the receiving apparatus 203 uses the asynchronous mode.

Figure 12:
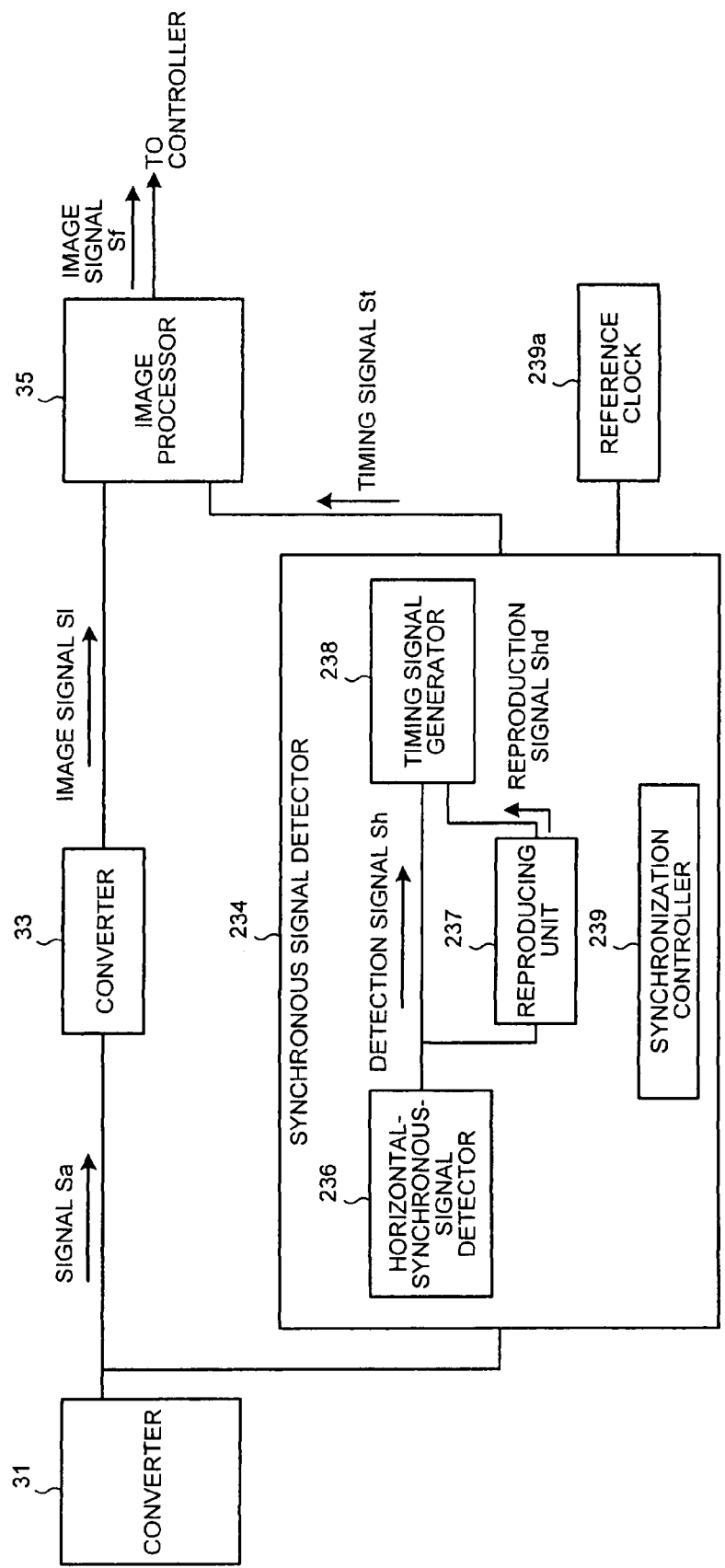
FIG. 12 is a block diagram of an essential configuration of the receiving apparatus shown in FIG. 11.

Next, the synchronous signal detector 234 in the external device 203b shown in FIG. 11 is described. FIG. 12 specifically describes components in relation to a detection of the horizontal synchronous signal and a generation of the timing signal St based on the horizontal synchronous signal, from among the components structuring the synchronous signal detector 234.

As shown in FIG. 12, the synchronous signal detector 234 includes a horizontal-synchronous-signal detector 236, a reproducing unit 237, a timing signal generator 238, and a synchronization controller 239 that controls the process operation for each of the components in the synchronous signal detector 234.

The horizontal-synchronous-signal detector 236 detects the horizontal synchronous signal corresponding to each of the scan lines from the signal Sa output from the receiving unit 31, and when detecting the horizontal synchronous signal, the horizontal-synchronous-signal detector 236 indicates that the horizontal synchronous signal is detected and outputs a detection signal Sh indicating the heading of the scan line component added with the horizontal synchronous signal to the timing signal generator 238. When the horizontal-synchronous-signal detector 236 detects more than a previously set predetermined portion among the signals structuring the horizontal synchronous signal from the signal Sa, even when the entire horizontal synchronous signal is not detected, the horizontal-synchronous-signal detector 236 outputs the detection signal Sh assuming that the horizontal synchronous signal is detected.

When the horizontal-synchronous-signal detector 236 does not detect the horizontal synchronous signal, the reproducing unit 237 generates a reproduction signal Shd corresponding to the scan line component, based on the horizontal synchronous signal detected by the horizontal-synchronous-signal detector 236 at a previous timing, and outputs the reproduction signal Shd to the timing signal generator 238. The reproducing unit 237 generates the reproduction signal Shd when the horizontal-synchronous-signal detector 236 does not detect the horizontal synchronous signal during a period from when the horizontal-synchronous-signal detector 236 generates the previous detection signal until the synchronous signal for the next scan line is detected. The reproduction signal Shd is for indicating the heading of the scan line component for which the horizontal synchronous signal is not detected. The reproducing unit 237 generates the reproduction signal Shd, based on an assumption that the radio signal is transmitted from the capsule endoscope 202 in accordance with a certain image line period TH and a certain horizontal blanking period Th, and on an assumption that the receiving apparatus 203 receives the radio signal in accordance with the image line period TH and the horizontal blanking period Th. With the above assumption, if the horizontal-synchronous-signal detector 236 does not output the detection signal Sh when an assumed period passed from when the horizontal-synchronous-signal detector 236 outputs the previous detection signal Sh until the next detection signal Sh is to be output, the reproducing unit 237 generates and outputs the reproduction signal Shd.

The timing signal generator 238 outputs the timing signal St that instructs a process start timing for the scan line component in the image signal Sl to the image processor 35, in response to an input timing of the scan line component in the image signal Sl, based on the detection signal Sh output from the horizontal-synchronous-signal detector 236 or the reproduction signal Shd output from the reproducing unit 237. The timing signal generator 238 outputs the timing signal St for every pixel image structuring one pixel, among the image signal Sl. The timing signal generator 238 sets a first output of the timing signal St based on the reproduction signal Shd ahead of a first output of the timing signal St based on the detection signal Sh, for a period for generating the reproduction signal in the reproducing unit 237. As a result, the timing signal generator 238 can accurately instruct the timing at which the image processor 35 processes the image signal positioned at the heading of the image signal Sl, both when the detection signal Sh is used and when the reproduction signal Shd is used.

Figure 13:
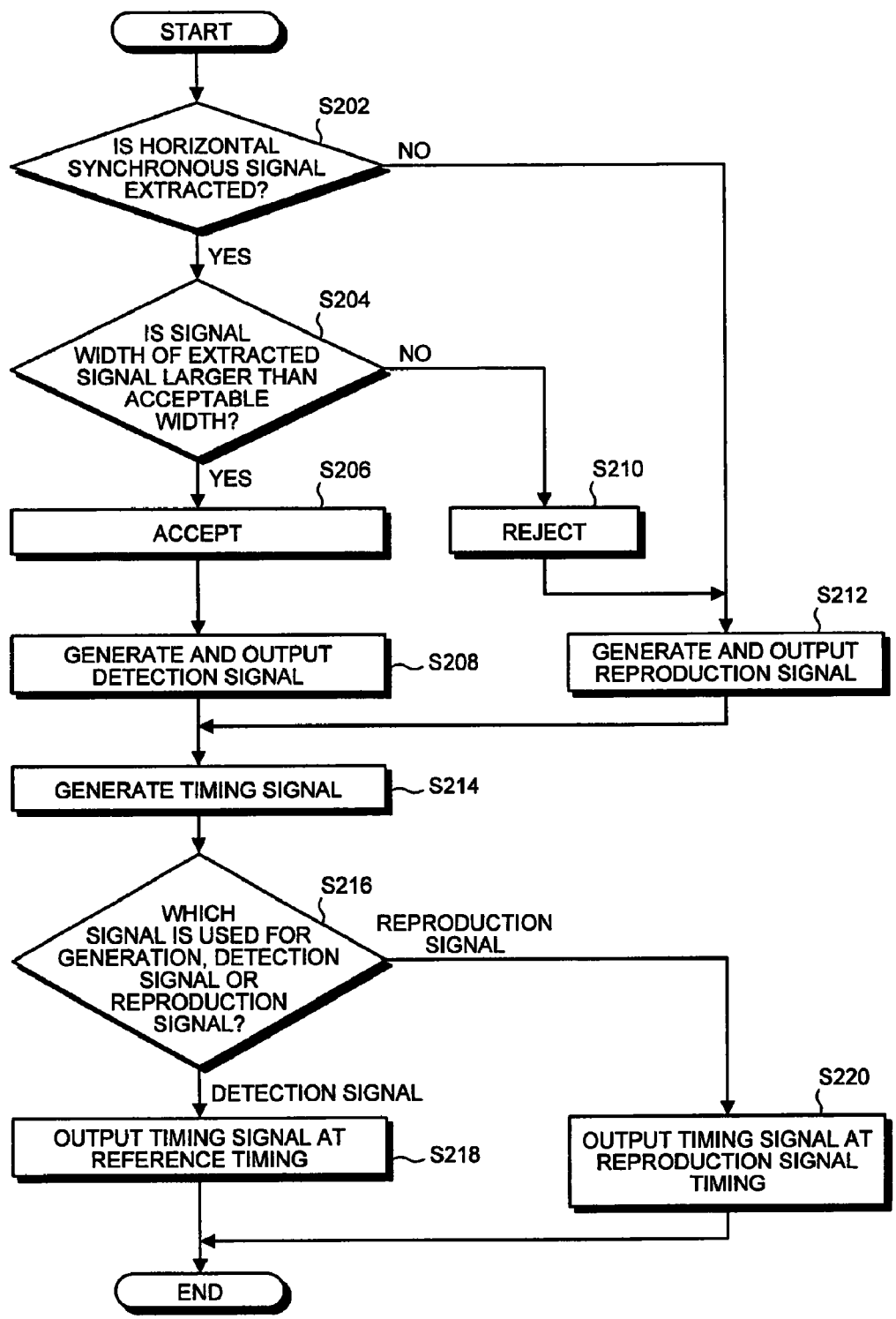
FIG. 13 is a flowchart for describing a process operation of a synchronous signal detector shown in FIG. 12.

Next, a process operation performed by the synchronous signal detector 234 to output the timing signal St based on the horizontal synchronous signal is described with reference to FIG. 13. As shown in FIG. 13, in the synchronous signal detector 234, the synchronization controller 239 determines whether the horizontal-synchronous-signal detector 236 has extracted the horizontal synchronous signal from the signal Sa (step S202).

When the synchronization controller 239 determines that the horizontal-synchronous-signal detector 236 has extracted the horizontal synchronous signal (step S202: Yes), the horizontal-synchronous-signal detector 236 determines whether a signal width of the horizontal synchronous signal is larger than a predetermined width, that is, the signal width of the extracted horizontal synchronous signal is larger than an acceptable width (step S204). When the horizontal-synchronous-signal detector 236 determines that the signal width of the extracted horizontal synchronous signal is larger than the acceptable width (step S204: Yes), the horizontal-synchronous-signal detector 236 accepts the extracted horizontal synchronous signal (step S206), generates the detection signal Sh, and outputs the detection signal Sh to the timing signal generator 238 (step S208). On the other hand, when the horizontal-synchronous-signal detector 236 determines that the signal width of the extracted horizontal synchronous signal is not larger than the acceptable width (step S204: No), the horizontal-synchronous-signal detector 236 does not accept the extracted horizontal synchronous signal (step S210), and proceeds to step S212. In this case, the horizontal-synchronous-signal detector 236 does not generate and output the detection signal Sh.

When the synchronization controller 239 determines that the horizontal-synchronous-signal detector 236 has not extracted the horizontal synchronous signal (step S202: No), or when the horizontal-synchronous-signal detector 236 does not accept the extracted horizontal synchronous signal (step S210) and does not generate the detection signal Sh, the synchronization controller 239 instructs the reproducing unit 237 to generate the reproduction signal Shd, and the reproducing unit 237 generates the reproduction signal Shd and outputs the reproduction signal Shd to the timing signal generator 238 (step S212).

The timing signal generator 238 generates the timing signal St by using the received detection signal Sh or the reproduction signal Shd (step S214). The synchronization controller 239 determines that the timing signal generator 238 generates the timing signal St by using whether the detection signal Sh or the reproduction signal Shd (step S216).

When the synchronization controller 239 determines that the timing signal generator 238 generates the timing signal St by using the detection signal Sh (step S216: detection signal), the synchronization controller 239 causes the timing signal generator 238 to output the timing signal St at a predetermined reference timing (step S218). With the reference timing, a period for generating the reproduction signal Shd in the reproducing unit 237 is not considered. The timing signal generator 238 outputs the timing signal St after a predetermined reference waiting period passes from the detection signal Sh is input from the reproducing unit 237, based on the reference timing, and thereafter, outputs the timing signal St at a certain output timing.

On the other hand, when the synchronization controller 239 determines that the timing signal generator 238 generates the timing signal St by using the reproduction signal Shd (step S216: reproduction signal), the synchronization controller 239 causes the timing signal generator 238 to output the timing signal St at a reproduction signal timing. With the reproduction signal timing, a period for generating the reproduction signal in the reproducing unit 237 is considered. The timing signal generator 238 outputs the timing signal St after a predetermined reproduction waiting period passes from the reproduction signal Shd is output from the reproducing unit 237, based on the reproduction signal timing, and thereafter, outputs the timing signal St at the certain output timing (step S220). The reproduction waiting period is such that a period from when the reproduction signal Shd is input until the timing signal St generated based on the reproduction signal Shd is output is compared to a period from when the detection signal Sh is input until the timing signal St generated based on the detection signal Sh is output, and a period corresponding to a period for generating the reproduction signal in the reproducing unit 237 is set ahead. As described, the timing signal generator 238 outputs the timing signal St by changing the output timing in response to either the detection signal Sh or the reproduction signal Shd.

Figure 14:
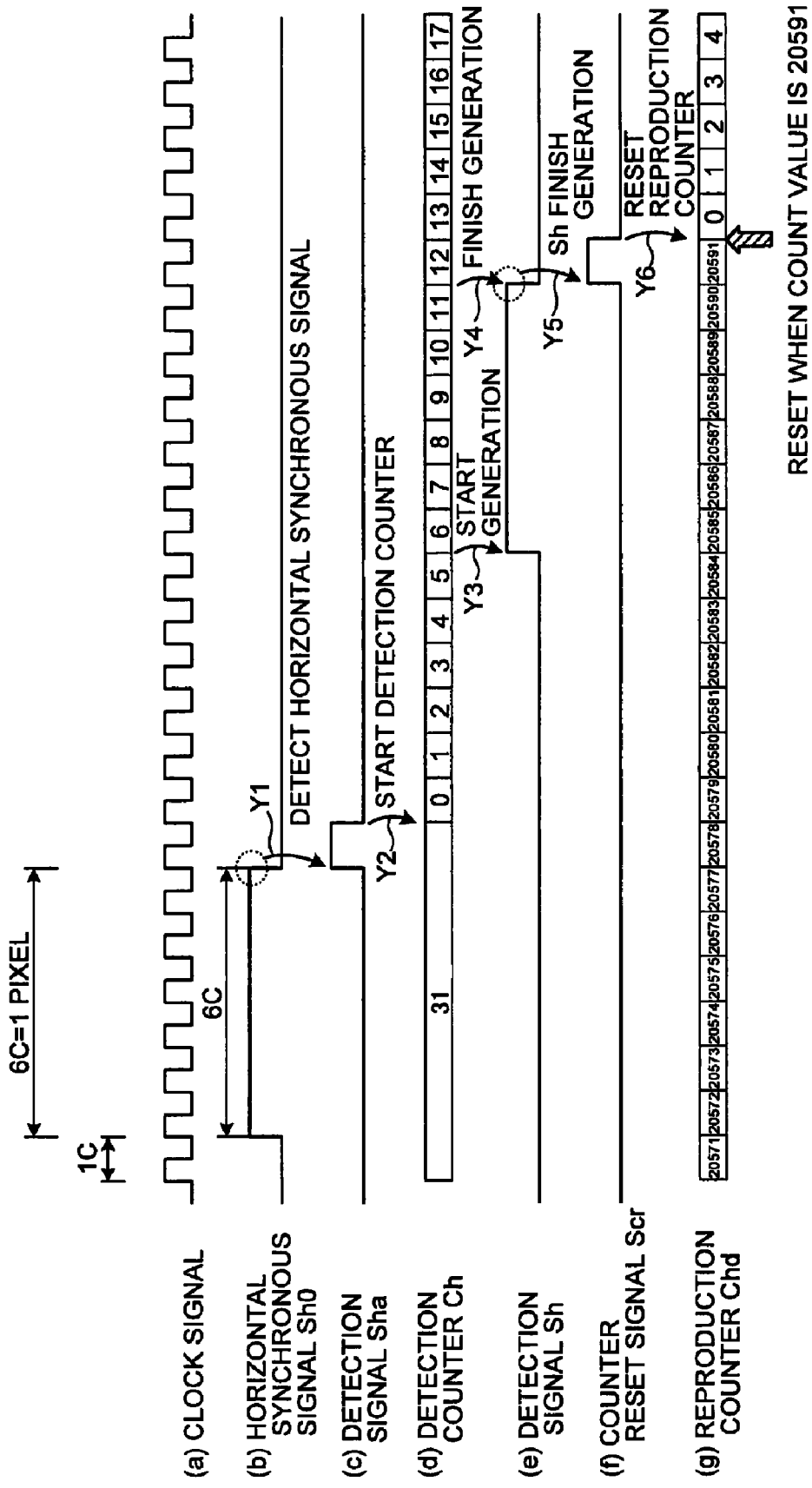
FIG. 14 is a timing chart for describing a detection-signal generation and an output process shown in FIG. 13.

Next, each of the processes described in FIG. 13 is described with reference to timing charts shown in the subsequent drawings from FIG. 14. First, a signal process performed by the horizontal-synchronous-signal detector 236 to output the detection signal Sh is described. FIG. 14 is a timing chart for each signal and each counter from when the horizontal-synchronous-signal detector 236 detects the horizontal synchronous signal until the detection signal Sh is output. In FIG. 14, (a) corresponds to a clock signal input from the reference clock 239a to the synchronization controller 239, and a signal for six clocks (6C) corresponds to a signal width of the pixel signal per one pixel of the signal Sa. (b) corresponds to a horizontal synchronous signal Sh0 extracted by the horizontal-synchronous-signal detector 236, (c) corresponds to a detection signal Sha output to the synchronization controller 239 when the horizontal-synchronous-signal detector 236 detects the horizontal synchronous signal Sh0, (d) corresponds to a count value of a detection counter Ch included in the synchronization controller 239 for generating the detection signal, (e) corresponds to the detection signal Sh generated by the horizontal-synchronous-signal detector 236, (f) corresponds to a counter reset signal Scr for a reproduction counter Chd included in the synchronization controller 239, and (g) corresponds to the count value of the reproduction counter Chd.

In FIG. 14, as shown with (b), when extracting the horizontal synchronous signal Sh0 corresponding to 6c (hereinafter, it is assumed for a description that an entire signal width of the horizontal synchronous signal Sh0 equivalents to 6c), the horizontal-synchronous-signal detector 236 detects a trailing portion of the horizontal synchronous signal Sh0 as shown with an arrow Y1, and outputs the detection signal Sha at a next clock of the trailing portion of the horizontal synchronous signal Sh0, as shown with (c). Thereafter, as shown with an arrow Y2, the synchronization controller 239 receives the detection signal Sha, resets the count value of the detection counter Ch to "0", and starts to count based on the clock signal. The horizontal-synchronous-signal detector 236 starts to generate and output the detection signal Sh when the count value of the detection counter Ch is "6" as shown with an arrow Y3, and stops generation and an output of the detection signal Sh when the count value is "11" as shown with an arrow Y4, under a control of the synchronization controller 239.

Namely, the horizontal-synchronous-signal detector 236 generates and outputs the detection signal Sh corresponding to 6c, after detecting the trailing portion of the detection signal Sh and counting 6C corresponding to one pixel. Thereafter, after generating the detection signal Sh as shown with an arrow Y5, that is, when the count value of the detection counter Ch is "12", the horizontal-synchronous-signal detector 236 outputs the counter reset signal Scr to the synchronization controller 239. The synchronization controller 239 receives the counter reset signal Scr, as shown with an arrow Y6, resets the count value "20591" of the reproduction counter Chd that has performed a count to "0", and starts to count based on the clock signal. The width between the count value "0" and "20591" corresponds to the image signal width of a single scan line including the horizontal synchronous signal. Accordingly, the synchronization controller 239 determines that the horizontal synchronous signal has been normally detected for the scan line, resets the count value of the reproduction counter Chd, and restarts to count of the reproduction counter Chd for determining the possibility of detecting the horizontal synchronous signal in the next scan line, based on the completion of the output of the detection signal Sh.

Figure 15:
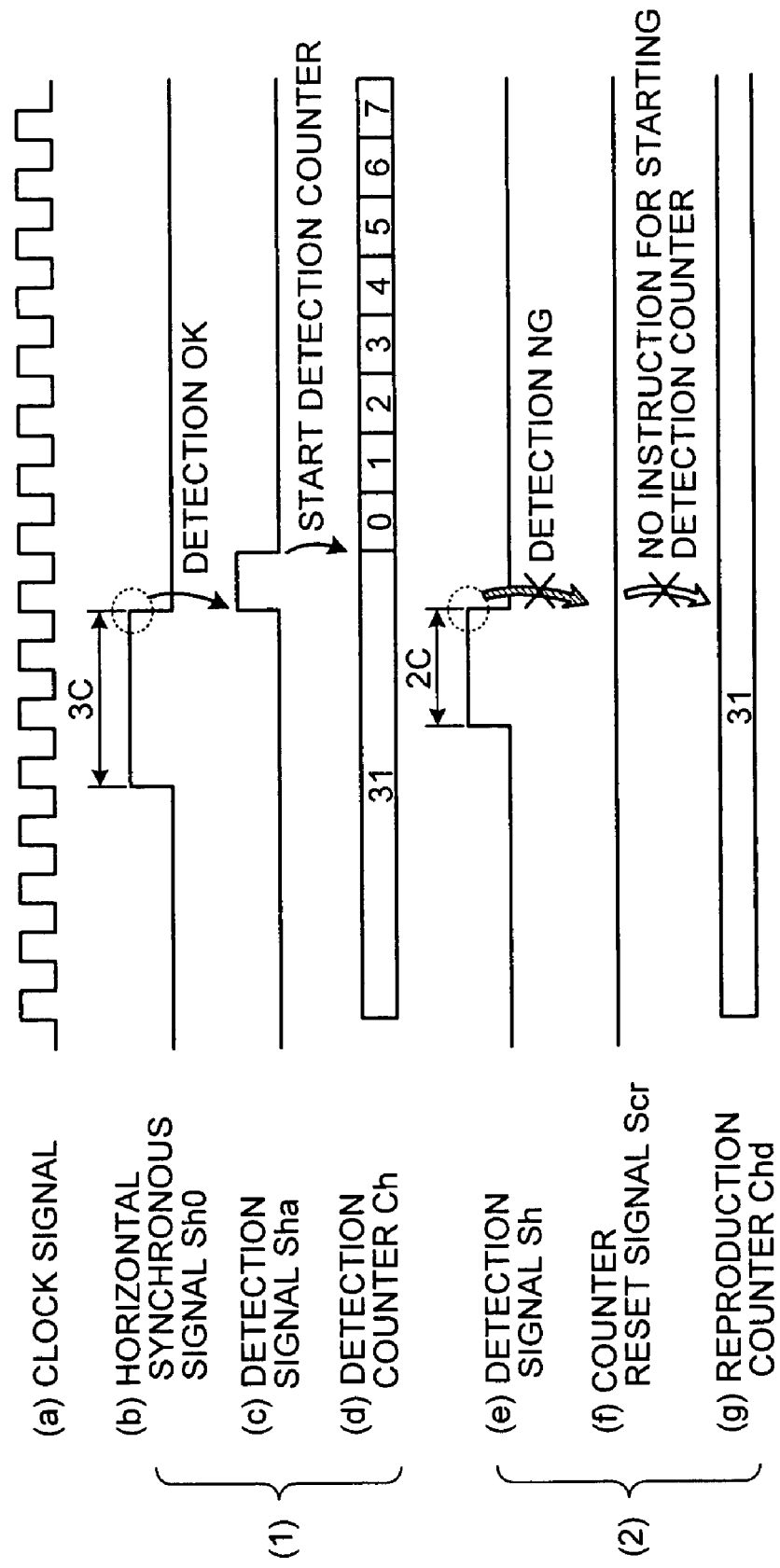
FIG. 15 is a timing chart for describing the detection-signal generation and the output process shown in FIG. 13.

The horizontal-synchronous-signal detector 236 generates the detection signal Sh by accepting the extracted horizontal synchronous signal, when the signal width of the extracted horizontal synchronous signal is larger than the acceptable signal width. For example, for the horizontal-synchronous-signal detector 236, when the extracted horizontal synchronous signal Sh0 is larger than the 3C width among the 6C width corresponding to the entire width of the horizontal synchronous signal, as shown in FIG. 15(1)(a), the synchronous signal detector 234 can accurately generate and output the timing signal St for the image processor 35. Accordingly, if the signal width of the horizontal synchronous signal Sh0 is larger than the 3C width, the horizontal-synchronous-signal detector 236 outputs the detection signal Sha, resets the detection counter Ch, and restarts the count. As a result, the horizontal-synchronous-signal detector 236 generates and outputs the detection signal Sh. However, as shown in FIG. 15(2)(e), with the horizontal-synchronous-signal detector 236, if the extracted horizontal synchronous signal Sh0 is smaller than the 2C among the 6C width corresponding to the entire width of the horizontal synchronous signal, it becomes difficult for the synchronous signal detector 234 to accurately generate and output the timing signal St for the image processor 35. Accordingly, when the signal width of the horizontal synchronous signal Sh0 is smaller than the 2C width, the horizontal-synchronous-signal detector 236 does not output the detection signal Sha and does not generate and output the detection signal Sh. As described, when the horizontal synchronous signal Sh0 having the signal width with which the accurate timing signal St can be generated and output, the synchronous signal detector 234 generates the timing signal St by not using the detection signal Sh but using the reproduction signal Shd generated and output by the reproducing unit 237.

Next, a signal process for generating and outputting the reproduction signal in the reproducing unit 237 is described with reference to a time chart shown in FIG. 16. Each of the timing charts (a) to (f) shown in FIG. 16 corresponds to the clock signal, the horizontal synchronous signal Sh0, the detection signal Sha, the count value of the detection counter Ch, the detection signal Sh, and the count value of the reproduction counter Chd, described in FIG. 14. FIG. 16(g) corresponds to the reproduction signal Shd generated by the reproducing unit 237 while (h) corresponds to the counter reset signal Scr described in FIG. 14.

In FIG. 16(b), as shown with an arrow Y7, when the horizontal synchronous signal Sh0 is not detected in the horizontal-synchronous-signal detector 236, the detection signal Sha is not detected and the count value of the detection counter Ch is not reset, as shown with (c) and an arrow Y8. As a result, as shown with (e) and an arrow Y9, the detection signal Sh is not output from the horizontal-synchronous-signal detector 236. In this case, in FIG. 16(e), as shown with an arrow Y11, even if the count value of the reproduction counter Chd is "20591", when determining that there is no instruction for the reset and the count start of the count value based on the counter reset signal Scr for the reproduction counter Chd, the synchronization controller 239 determines that the horizontal synchronous signal is not detected in the horizontal-synchronous-signal detector 236 and instructs the reproducing unit 237 to generate the reproduction signal Shd. The case when the count value of the reproduction counter Chd is "20591" corresponds to such a case that a period corresponding to the image signal width for the one scan line has passed. When the count value is "20591", if the horizontal synchronous signal Sh0 is normally detected, as shown in FIG. 14, it is because the generation and the output of the detection signal Sh and the output of the counter reset signal Scr have been completed. Therefore, if the counter reset signal Scr is not received when the count value of the reproduction counter Chd is "20591", the synchronization controller 239 determines that the horizontal-synchronous-signal detector 236 has not been able to detect the horizontal synchronous signal Sh0 and the detection signal Sh has not been output until this timing.

In this case, the reproducing unit 237 starts to generate and output the reproduction signal Shd when the count value is "20597" that is after the 6c width including the count value "20591" of the reproduction counter Chd as shown with an arrow Y12, and stops the generation and the output of the reproduction signal Shd when the count value is "20602" as shown with an arrow Y13, under a control of the synchronization controller 239. Thereafter, as shown in FIG. 14, a reproducing unit 237 outputs the counter reset signal Scr to the synchronization controller 239 after the generation of the reproduction signal is finished. The synchronization controller 239 receives the counter reset signal, as shown with an arrow Y15, resets the count value of the reproduction counter Chd to "0", and thereafter, causes the reproduction counter Chd to start to count.

Figure 16:
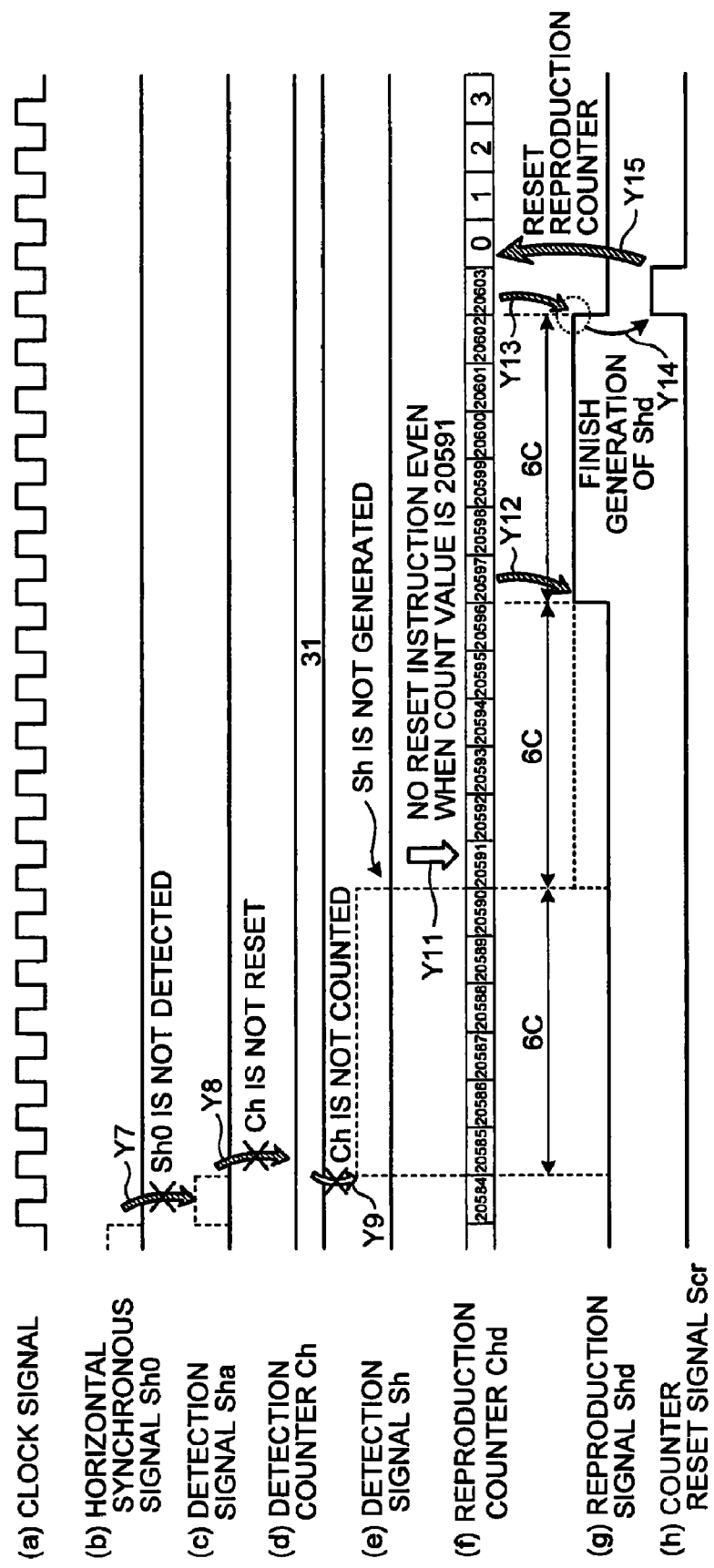
FIG. 16 is a timing chart for describing a reproduction-signal generation and an output process shown in FIG. 13.

As shown in FIG. 16, the reproducing unit 237 generates and outputs the reproduction signal at a late timing for a 12C width, that is, the signal width corresponding to 2 pixels, compared to the case when the detection signal Sh is output from the horizontal-synchronous-signal detector 236.

It is required to absorb the generation and the output of the reproduction signal Shd at the late timing. Accordingly, when the reproducing unit 237 generates the reproduction signal Shd and generates and outputs the reproduction signal Shd2 for the scan line component next to the output scan line component, the reproducing unit 237 generates and outputs the reproduction signal at an earlier timing for a period corresponding to the signal width of the 2 pixels. More specifically, as shown with an arrow Y21 in FIG. 17(f)(g2), the reproducing unit 237 starts to generate and output the reproduction signal Shd2 when the count value is "20584", which is a timing 12C width earlier than the timing for generating the reproduction signal Shd that is firstly generated, in response to the scan line next to the output scan line. As described, the reproducing unit 237 generates the reproduction signal Shd2 at the timing 12C width earlier, that is, an earlier timing for the period corresponding to the signal width of the 2 pixels. Then, as shown with an arrow Y23, the reproducing unit 237 stops the generation and the output of the regeneration signal Shd2 when the count value is "20590" that is 6C width behind from the count value "20584". Thereafter, the reproducing unit 237 outputs the counter reset signal Scr to the synchronization controller 239 after the generation of the reproduction signal Shd2 is finished. The synchronization controller 239 receives the counter reset signal Scr, resets the count value of the reproduction counter Chd to "0", and causes the reproduction counter Chd to start the counting, as shown with an arrow Y24.

Next, a signal process for generating the timing signal St in the timing signal generator 238 is described with reference to a time chart shown in FIG. 18. FIG. 18(1) corresponds to a case in which the timing signal generator 238 generates the timing signal St by using the detection signal Sh, (a) corresponds to the detection signal Sh, (b) corresponds to a reset signal Str for instructing the reset of the count value and the count start for a timing counter Ct in the timing signal generator 238, (c) corresponds to the count value of the timing counter Ct, (d) corresponds to the timing signal St generated by the timing signal generator 238, and (e) corresponds to a data signal in each of the scan lines of the image signal Sl output from the converter 33. FIG. 18(2) corresponds to a case in which the timing signal generator 238 generates the timing signal St by using the reproduction signal Shd, (f) corresponds to the reproduction signal Shd, (g) corresponds to the reset signal Str, (h) corresponds to the count value of the timing counter Ct, (i) corresponds to the timing signal St, and (j) corresponds to the data signal. In FIG. 18, each of the signals and each of the counters are processed based on the clock signal shown with (A). The timing counter Ct starts counting from the count value "0", and when proceeded to the count value "5", the count value is automatically reset to "0", and the count is to be continued. Among the signals Sa input to the converter 33, as shown with the data signals (e) and (j) indicating each of the pixel information, the signal width of 6C is included per one pixel, and the timing counter Ct performs the count in response to the signal width per one pixel.

First, the case in which the timing signal generator 238 generates the timing signal St by using the detection signal Sh is described with reference to FIG. 18(1). In FIG. 18(a), when detecting the reception of the detection signal Sh, the timing signal generator 238 outputs the reset signal Str shown with (b) to the timing counter Ct, as shown with an arrow Y31. As a result, as shown with an arrow Y32, the count value of the timing counter Ct shown with (c) is reset to "0", and thereafter, the count is continued. The timing signal generator 238 generates the reset signal Str while the count value of the timing counter Ct is "1", as shown with an arrow Y33 and (d). In this case, as shown with an arrow Y34, before the count value of the timing counter Ct is again to be "1", that is, in response to the next pixel in the data signal, the next reset signal Str is generated. As described, the timing signal generator 238 sequentially generates the timing signal St with respect to each pixel unit of the data signal, in response to the count value "1" of the timing counter Ct. The reset signal Str is output to reset the timing counter Ct at a substantial center of the signal width for every one pixel of the data signal. The substantial center of the signal width for every one pixel of the data signal corresponds to the information main frame that indicates a luminance of the pixel. Therefore, the synchronous signal detector 234 generates the timing signal St at the substantial center of the signal width for every one pixel of the data signal and instructs the image processor 35 to perform the processes, and the image processor 35 can assuredly acquire the luminous information of the pixel.

Next, the case in which the timing signal generator 238 generates the timing signal St by using the reproduction signal Shd is described with reference to FIG. 18(2). The timing signal generator 238, similar to the case shown in FIG. 18(1), outputs the reset signal Str as shown with an arrow Y36 and (g), when detecting the reception of the reproduction signal Shd as shown with (f). As a result, as shown with an arrow Y37, the count value of the reset counter Ctr with (h) is reset, and the timing signal generator 238 generates the timing signal St with respect to each one pixel unit of the data signal, as shown with arrows Y38, Y39, and (i). The timing signal generator 238 converts the generated timing signal St to be corresponding to the signal format of the image signal Sl output from the converter 33, and thereafter, outputs to the image processor 35. For example, when the signal Sa input to the converter 33 is in a serial format and the converter 33 processes the signal Sa to output the image signal Sl in a parallel format, the timing signal generator 238 converts the generated timing signal St to be corresponding to the parallel format.

As shown with (a) and (f), the reproduction signal Shd is input to the timing signal generator 238 at a timing behind in 12C corresponding to 2 pixels compared to the detection signal Sh. As a result, when generating the timing signal St by using the reproduction signal Shd, the timing signal generator 238 generates the timing signal St at a timing behind in 2 pixels, compared to the case of generating the timing signal St by using the detection signal Sh. As a result, the synchronization controller 239 needs to change the output timing between the timing signal St generate by using the detection signal Sh and the timing signal St generated by using the reproduction signal Shd, so that the timing signal generator 238 causes the image processor 35 to output the timing signal St at a timing corresponding to the timing at which the image signal Sl is input to the image processor 35. Namely, as described at step S218 and step S220 in FIG. 13, the timing signal generator 238 outputs the timing signal St based on the detection signal Sh by using the reference timing, and outputs the timing signal St based on the reproduction signal Shd by using the reproduction signal timing.

The reference timing and the reproduction signal timing at which the timing signal St is output from the timing signal generator 238 are described with reference to FIG. 19. FIG. 19(a) represents the count value of an output counter Co included in the synchronization controller 239. The output counter Co starts to count based on the reception of either the detection signals Sh or the reproduction signal Shd, and counts with respect to each signal width corresponding to the one pixel of the image signal Sl output from the converter 33. When proceeded to the count value "9", the output counter Co resets the count value to "0" and continues to count. FIG. 19(b) corresponds to an output instruction signal Si corresponding to the timing signal St generated based on the detection signal Sh, among the output instruction signal output from the synchronization controller 239 to the timing signal generator 239. Namely, the output instruction signal Si corresponds to the reference timing. FIG. 19(c) corresponds to an output instruction signal Sid corresponding to the timing signal St generated based on the reproduction signal Shd. Namely, the output instruction signal Sid corresponds to the reproduction signal timing. (b) and (c) represent cases in which the timing signal St is output with Duty ratio of 50%.

As shown in FIG. 19(b), for the timing signal St based on the detection signal Sh, for example, the synchronization controller 239 outputs the output instruction signal Si between the count value "3" and the count value "7", and instructs the timing signal generator 238 to output the timing signal St. In this case, the timing signal generator 238 outputs the timing signal St to the image processor 35, between the count value "3" and the count value "7", based on the instruction of the output instruction signal Si. As described, the timing signal generator 238 outputs the timing signal St from the count value "3" of the output counter Ct, by using the reference timing.

On the other hand, as shown in FIG. 19(c), for the timing signal St based on the reproduction signal Shd, the synchronization controller 239 outputs the output instruction signal Sid between the count value "1" and the count value "5", which is two counts earlier than the output instruction signal Si, and instructs the timing signal generator 238 to output the timing signal St. As described, the timing signal St generated based on the reproduction signal Shd is output at the timing for absorbing the delay of inputting the reproduction signal Shd. Namely, the period from when the reproduction signal Shd is input until the timing signal St generated based on the reproduction signal Shd is output is compared to the period from when the detection signal Sh is input until the timing signal St generated based on the detection signal Sh is output, and a period corresponding to a period for generating the reproduction signal in the reproducing unit 237, that is, a period corresponding to 2 pixels is set ahead.

As described, the synchronization controller 239 causes the timing signal generator 238 to output the timing signal St to the image processor 35 at a timing corresponding to a timing at which the detection signal Sh and the reproduction signal Shd are input to the timing signal generator 238. Accordingly, the synchronous signal detector 234 enables to output both the timing signal St using the detection signal Sh and the timing signal St using the reproduction signal Shd to the image processor 35 at a timing corresponding to the timing at which the image signal Sl is input to the image processor 35, and can accurately instruct the image processing timing for the image processor 35.

The receiving apparatus 203 according to the second embodiment enables to generate the reproduction signal based on the previously detected horizontal synchronous signal, when the horizontal synchronous signal is not detected from the radio signal transmitted in the asynchronous mode, to perform the process synchronization for the scan line component by using the reproduction signal, and therefore enables to accurately process the information component of the received radio signal. Therefore, the receiving apparatus 203 according to the second embodiment can perform the image process for the image signal corresponding to the scan line for which the horizontal synchronous signal is not detected, and can accurately acquire the image information corresponding to one image. As a result, the receiving apparatus 203 can accurately provide a user with the body cavity image captured by the capsule endoscope, and it becomes possible to support the accurate diagnosis made by the user.

Although the case in which the timing signal generator 238 changes the output timing of the timing signal St in response to the case in which the detection signal Sh or the reproduction signal Shd is used, the present invention is not thus limited, and it is acceptable that the horizontal-synchronous-signal detector 236 outputs the detection signal Sh to the timing signal generator 238 depending on the timing at which the reproduction signal Shd is output from the reproducing unit 237. In this case, the timing signal generator 238 can output the timing signal St depending on the input timing of the image signal Sl to the processor 35.

Industrial Applicability

As described above, the receiving apparatus and the in-vivo information acquiring system according to the present invention is suitable for transmitting a radio signal including at least an main frame portion of information to an outside, and for processing the transmitted radio signal, and more specifically suitable for processing image information corresponding to each of images captured by an body insertable apparatus such as a capsule endoscope.

The invention claimed is:

1. A transmitting apparatus that transmits a radio signal including at least main frame portion of information to a receiving apparatus, the transmitting apparatus comprising:
   an information main-frame output unit that outputs the main frame portion of information;
   a storage unit that stores identification information indicating use of the radio signal;
   a selector that selects a synchronous mode based on the identification information;
   a reference signal generator that generates a reference signal including a different signal level based on the synchronous mode selected by the selector, and outputs a reference signal component including at least the reference signal;
   an inserting unit that inserts the reference signal component into a predetermined heading period of the main frame portion of information and at least a part of a blanking period in which a signal component does not exist, and outputs a resulting signal; and
   a radio transmitting unit that wirelessly transmits the resulting signal output from the inserting unit as the radio signal to the receiving apparatus, wherein
   a frequency of the transmitted radio signal and a frequency of a process reference clock which is a process reference for the radio signal are synchronized in the receiving apparatus, based on the reference signal component included in the radio signal transmitted from the transmitting apparatus, wherein the selector selects the frequency of the reference signal based on instruction information for instructing whether the reference signal component is inserted and the frequency of the reference signal, and wherein the reference signal generator generates the reference signal with the frequency selected by the selector.

2. The transmitting apparatus according to claim 1, further comprising:
   a timing generator that controls an output timing of the main frame portion of information in the information main-frame output unit and correlates an output timing of the reference signal component in the reference signal generator with the predetermined heading period of the main frame portion of information output from the information main-frame output unit and at least a part of the blanking period.

3. The transmitting apparatus according to claim 1, wherein
   the storage unit stores the instruction information, and the selector selects whether the reference signal component is inserted and the frequency of the reference signal, based on the instruction information stored in the storage unit.

4. The transmitting apparatus according to claim 1, further comprising:
   an information acquiring unit that acquires predetermined information to be a process target in the information main-frame output unit and outputs the acquired predetermined information to the information main-frame output unit, wherein the information main-frame output unit processes the information output from the information acquiring unit and thereafter outputs the processed information as the main frame portion of information, and the selector selects one of a frequency corresponding to a frequency of the main frame portion of information output from the information main-frame output unit and a frequency corresponding to a frequency of the predetermined information output from the information acquiring unit, as the frequency of the reference signal based on the instruction information.

5. The transmitting apparatus according to claim 1, wherein
   the main frame portion of information is an image signal, the blanking period is a horizontal blanking period, and the predetermined heading period includes a vertical synchronous signal.

6. The transmitting apparatus according to claim 1, wherein
   the transmitting apparatus has a function for acquiring in-vivo information when inserted into a subject, and the main frame portion of information is formed by including the in-vivo information.

7. A receiving apparatus that processes the information component among the radio signal received by an antenna, the receiving apparatus comprising:
   an antenna for receiving a radio signal including a predetermined unit of an information component that structures a main frame portion of information;
   a detector that detects a synchronous signal added to the information component with respect to each information component, generates a detection signal indicating a heading of the information component when the synchronous signal is detected, and generates a reproduction signal indicating the heading of the information component based on the previously generated detection signal when the synchronous signal is not detected;
   a timing signal output unit that outputs a timing signal that instructs a process start timing of the information component in response to an input timing of the information component, based on either the detection signal or the reproduction signal generated by the detector; and
   a processor that initiates a process of the information component in synchronization with the input timing of the information component, based on the timing signal output from the timing signal output unit.

8. The receiving apparatus according to claim 7, wherein the detector outputs the detection signal when a portion larger than a predetermined portion is detected from the entire synchronous signal.

9. The receiving apparatus according to claim 7, wherein the detector generates the reproduction signal when the synchronous signal is not detected during a period from when a previous detection signal is generated until the synchronous signal for a next information component is to be detected.

10. The receiving apparatus according to claim 7, wherein the timing signal output unit sets a first output of the timing signal generated based on the reproduction signal ahead of a first output of the timing signal generated based on the detection signal by a period for generating the reproduction signal by the detector.

11. The receiving apparatus according to claim 7, wherein the radio signal includes an image signal,
   the information component is a scan line component that structures the image signal, and
   the synchronous signal is a horizontal synchronous signal.

12. The receiving apparatus according to claim 7, wherein the radio signal is formed by including in-vivo information acquired by a transmitting apparatus that is inserted into a subject.

13. The transmitting apparatus according to claim 2, Wherein
the storage unit stores the instruction information for instructing whether the reference signal component is inserted and the frequency of the reference signal, and
the selector selects whether the reference signal component is inserted and the frequency of the reference signal based on the instruction information stored in the storage unit.

14. The transmitting apparatus according to claim 2, further comprising:
an information acquiring unit that acquires predetermined information to be a process target in the information main-frame output unit and outputs the acquired predetermined information to the information main-frame output unit, wherein
the information main-frame output unit processes the information output from the information acquiring unit and thereafter outputs the processed information as the main frame portion of information, and
the selector selects one of a frequency corresponding to a frequency of the main frame portion of information output from the information main-frame output unit and a frequency corresponding to a frequency of the predetermined information output from the information acquiring unit, as the frequency of the reference signal based on instruction information for instructing whether the reference signal component is inserted and the frequency of the reference signal.

15. The transmitting apparatus according to claim 3, further comprising:
an information acquiring unit that acquires predetermined information to be a process target in the information main-frame output unit and outputs the acquired predetermined information to the information main-frame output unit, wherein
the information main-frame output unit processes the information output from the information acquiring unit and thereafter outputs the processed information as the main frame portion of information, and
the selector selects one of a frequency corresponding to a frequency of the main frame portion of information output from the information main-frame output unit and a frequency corresponding to a frequency of the predetermined information output from the information acquiring unit, as the frequency of the reference signal based on the instruction information.

16. A method of transmitting and receiving a radio signal including at least main frame portion of information, the method comprising:
outputting the main frame portion of information;
storing identification information indicating use of the radio signal;
selecting a synchronous mode based on the identification information;
selecting a frequency of a reference signal based on instruction information for instructing whether a reference signal component is inserted and the frequency of the reference signal;
generating the reference signal including a different signal level based on the synchronous mode selected in the selecting, and outputting the reference signal component including at least the reference signal, the reference signal having a frequency equal to the selected frequency;
inserting the reference signal component into a predetermined heading period of the main frame portion of information and at least a part of a blanking period in which a signal component does not exist, and outputting a resulting signal; and
transmitting wirelessly the resulting signal output in the outputting as the radio signal to a receiving apparatus, wherein
a frequency of the transmitted radio signal and a frequency of a process reference clock which is a process reference for the radio signal are synchronized in the receiving apparatus, based on the reference signal component included in the radio signal transmitted in the transmitting.

17. A method of processing an information component included in a radio signal including a predetermined unit of an information component that structures a main frame portion of information, the method comprising:
detecting a synchronous signal added to the information component with respect to each information component, generating a detection signal indicating a heading of the information component when the synchronous signal is detected, and generating a reproduction signal indicating the heading of the information component based on the previously generated detection signal when the synchronous signal is not detected; and
outputting a timing signal that instructs a process start timing of the information component in response to an input timing of the information component, based on either the detection signal or the reproduction signal generated in the detecting, wherein
a process of the information component in synchronization with the input timing of the information component is initiated, based on the timing signal output from the outputting.

* * * * *